United States Patent
Osafune et al.

(10) Patent No.: US 9,796,962 B2
(45) Date of Patent: Oct. 24, 2017

(54) METHOD FOR GENERATING PANCREATIC HORMONE-PRODUCING CELLS

(71) Applicant: Kyoto University, Kyoto (JP)

(72) Inventors: Kenji Osafune, Kyoto (JP); Nobuya Inagaki, Kyoto (JP); Taro Toyoda, Kyoto (JP); Yasushi Kondo, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 61 days.

(21) Appl. No.: 14/909,690

(22) PCT Filed: Aug. 6, 2014

(86) PCT No.: PCT/JP2014/070787
§ 371 (c)(1),
(2) Date: May 24, 2016

(87) PCT Pub. No.: WO2015/020113
PCT Pub. Date: Feb. 12, 2015

(65) Prior Publication Data
US 2016/0289642 A1    Oct. 6, 2016

(30) Foreign Application Priority Data

Aug. 7, 2013  (JP) ................. 2013-164137

(51) Int. Cl.
*C12N 5/071*   (2010.01)

(52) U.S. Cl.
CPC ........ *C12N 5/0676* (2013.01); *C12N 2500/38* (2013.01); *C12N 2501/01* (2013.01); *C12N 2501/15* (2013.01); *C12N 2501/155* (2013.01); *C12N 2501/16* (2013.01); *C12N 2501/385* (2013.01); *C12N 2501/39* (2013.01); *C12N 2501/727* (2013.01); *C12N 2501/82* (2013.01); *C12N 2501/999* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | |
|---|---|---|
| 4,326,055 A | 4/1982 | Loeliger |
| 5,234,926 A | 8/1993 | Chandraratna |
| 5,843,780 A | 12/1998 | Thomson |
| 7,534,608 B2 | 5/2009 | Martinson et al. |
| 8,048,999 B2 | 11/2011 | Yamanaka et al. |
| 8,791,248 B2 | 7/2014 | Yamanaka et al. |
| 8,877,493 B2 | 11/2014 | Sekiguchi et al. |
| 8,932,853 B2 | 1/2015 | Hosoya et al. |
| 9,127,256 B2 | 9/2015 | Fusaki et al. |
| 9,157,069 B2 | 10/2015 | Hosoya et al. |
| 2003/0087919 A1 | 5/2003 | Nagarathnam et al. |
| 2003/0125344 A1 | 7/2003 | Nagarathnam et al. |
| 2004/0002507 A1 | 1/2004 | Nagarathnam et al. |
| 2004/0002508 A1 | 1/2004 | Nagarathnam et al. |
| 2004/0014755 A1 | 1/2004 | Nagarathnam et al. |
| 2005/0192304 A1 | 9/2005 | Nagarathnam et al. |
| 2005/0209261 A1 | 9/2005 | Nagarathnam et al. |
| 2008/0213885 A1 | 9/2008 | Tryggvason et al. |
| 2011/0070647 A1 | 3/2011 | Dezawa et al. |
| 2011/0117645 A1 | 5/2011 | Yasuda et al. |

FOREIGN PATENT DOCUMENTS

| | | |
|---|---|---|
| EP | 2 096 169 A1 | 9/2009 |
| JP | 2006-075022 A | 3/2006 |
| JP | 2009-225661 A | 10/2009 |
| WO | 02/076976 A2 | 10/2002 |
| WO | 03/059913 A1 | 7/2003 |
| WO | 03/062225 A1 | 7/2003 |
| WO | 03/062227 A1 | 7/2003 |
| WO | 2004/039796 A1 | 5/2004 |
| WO | 2007/069666 A1 | 6/2007 |
| WO | 2008/118820 A2 | 10/2008 |
| WO | 2008/144690 A2 | 11/2008 |
| WO | 2009/007852 A2 | 1/2009 |
| WO | 2009/032194 A1 | 3/2009 |
| WO | 2009/048675 A1 | 4/2009 |
| WO | 2009/057831 A1 | 5/2009 |
| WO | 2009/058413 A1 | 5/2009 |
| WO | 2009/075119 A1 | 6/2009 |
| WO | 2009/079007 A1 | 6/2009 |
| WO | 2009/091659 A2 | 7/2009 |
| WO | 2009/101084 A1 | 8/2009 |
| WO | 2009/101407 A2 | 8/2009 |
| WO | 2009/102983 A2 | 8/2009 |
| WO | 2009/114949 A1 | 9/2009 |
| WO | 2009/117439 A2 | 9/2009 |
| WO | 2009/123349 A1 | 10/2009 |
| WO | 2009/126250 A2 | 10/2009 |
| WO | 2009/126251 A2 | 10/2009 |

(Continued)

OTHER PUBLICATIONS

Takahashi et al. (2009) "Human Induced Pluripotent Stem Cells on Autologous Feeders," PLoS One. 4:e8067. pp. 1-6.

Thomson et al (1996) "Pluripotent cell lines derived from common marmoset (*Callithrix jacchus*) blastocysts," Biol. Reprod. 55:254-259.

Thomson et al. (1995) "Isolation of a primate embryonic stem cell line," Proc. Natl. Acad. Sci. USA. 92:7844-7848.

Thomson et al. (1998) "Embryonic stem cell lines derived from human blastocysts," Science 282:1145-1147.

Thomson et al. (1998) "Primate embryonic stem cells," Curr. Top. Dev. Biol. 38:133-165.

Uehata et al. (1997) "Calcium sensitization of smooth muscle mediated by a Rho-associated protein kinase in hypertension," Nature. 389:990-994.

(Continued)

*Primary Examiner* — David Berke-Schlessel
(74) *Attorney, Agent, or Firm* — Lathrop Gage LLP; James H. Velema, Esq.

(57) ABSTRACT

Provided is a method for inducing pancreatic hormone-producing cells from pancreatic progenitor cells efficiently. The method comprises a step of culturing the cells in a culture medium comprising sodium cromoglicate.

20 Claims, 12 Drawing Sheets

(56) References Cited

FOREIGN PATENT DOCUMENTS

| WO | 2009/126655 A2 | 10/2009 |
|---|---|---|
| WO | 2009/146408 A1 | 12/2009 |
| WO | 2009/157593 A1 | 12/2009 |
| WO | 2010/008054 A1 | 1/2010 |
| WO | 2010/009015 A2 | 1/2010 |
| WO | 2010/013845 A1 | 2/2010 |
| WO | 2010/033906 A2 | 3/2010 |
| WO | 2010/033920 A2 | 3/2010 |
| WO | 2010/037784 A1 | 4/2010 |
| WO | 2010/042800 A1 | 4/2010 |
| WO | 2010/050626 A1 | 5/2010 |
| WO | 2010/056831 A2 | 5/2010 |
| WO | 2010/068955 A2 | 6/2010 |
| WO | 2010/098419 A1 | 9/2010 |
| WO | 2010/102267 A2 | 9/2010 |
| WO | 2010/111409 A2 | 9/2010 |
| WO | 2010/111422 A2 | 9/2010 |
| WO | 2010/115050 A2 | 10/2010 |
| WO | 2010/124290 A2 | 10/2010 |
| WO | 2010/147395 A2 | 12/2010 |
| WO | 2010/147612 A1 | 12/2010 |
| WO | 2010137746 A1 | 12/2010 |
| WO | 2011/007900 A1 | 1/2011 |
| WO | 2011/043405 A1 | 4/2011 |
| WO | 2011/081222 A1 | 7/2011 |
| WO | 2012/020845 A1 | 2/2012 |

OTHER PUBLICATIONS

Ueno et al. (2006) "Neural conversion of ES cells by an inductive activity on human amniotic membrane matrix," Proc. Natl. Acad. Sci. USA. 103:9554-9559.

Wakayama et al. (2001) "Differentiation of embryonic stem cell lines generated from adult somatic cells by nuclear transfer," Science. 292:740-743.

Wakayama et al. (2005) "Establishment of male and female nuclear transfer embryonic stem cell lines from different mouse strains and tissues," Biol. Reprod. 72:932-936.

Wakayama et al. (2008) "[ES Cells by Nuclear Implantation]," Experimental Medicine]. 26(5):47-52. 若山清香, 引地 貴亮, 若山照彦 (2008) " 核移植によるES細胞," 実験医学増刊. 26(5):47-52.—with English machine translation.

Warren et al. (2010) "Highly efficient reprogramming to pluripotency and directed differentiation of human cells with synthetic modified mRNA," Cell Stem Cell. 7:618-630.

Yoshida et al. (2009) "Hypoxia enhances the generation of induced pluripotent stem cells," Cell Stem Cell. 5:237-241.

Yu et al. (2007) "Abstract 381: Dorsomorphin, A Novel Inhibitor of Bone Morphogenetic Protein Signaling," Circulation. 116(Suppl 16). Abstract 381.

Yu et al. (2007) "Induced pluripotent stem cell lines derived from human somatic cells," Science. 318:1917-1920.

Yu et al. (2008) "Dorsomorphin inhibits BMP signals required for embryogenesis and iron metabolism," Nat. Chem. Biol. 4:33-41.

Zhao et al. (2008) "Two supporting factors greatly improve the efficiency of human iPSC generation," Cell Stem Cell. 3:475-479.

International Search Report with Written Opinion corresponding to International Patent Application No. PCT/JP2014/070787, mailed Nov. 11, 2014.

Stadtfeld et al. (2008) "Induced pluripotent stem cells generated without viral integration," Science. 322:945-949.

Hosoya (2012) "Preparation of pancreatic β-cells from human iPS cells with small molecules," Islets. 4(3):249-252.

Kim et al. (2012) "In vivo antitumor effect of cromolyn in PEGylated liposomes for pancreatic cancer," J. Controlled Release. 157:190-195.

Search Report corresponding to European Patent Application No. 14834263.7, dated Mar. 22, 2017.

Byrne et al. (2007) "Producing primate embryonic stem cells by somatic cell nuclear transfer," Nature. 450:497-502.

Cibelli et al. (1998) "Transgenic bovine chimeric offspring produced from somatic cell-derived stem-like cells," Nature Biotechnol. 16:642-646.

D'Amour et al. (2006) "Production of pancreatic hormone-expressing endocrine cells from human embryonic stem cells," Nature Biotechnology. 24(11)1392-1401.

Eminli et al. (2008) "Reprogramming of neural progenitor cells into induced pluripotent stem cells in the absence of exogenous Sox2 expression," Stem Cells. 26:2467-2474.

Evans et al. (1981) "Establishment in culture of pluripotential cells from mouse embryos," Nature. 292:154-156.

Feng et al. (2009) "Reprogramming of fibroblasts into induced pluripotent stem cells with orphan nuclear receptor Esrrb," Nat. Cell. Biol. 11:197-203.

Genbank Database [online] (Jun. 6, 2016) "*Homo sapiens* chromosome 1, alternate assembly CHM1_1.1, whole genome shotgun sequence," Accession Nos. NC_018912. National Center for Biotechnology Information. Accessible on the Internet at URL: http://www.ncbi.nlm.nih.gov/nuccore/528476670. [Last Accessed Sep. 16, 2016].

Genbank Database [online] (Sep. 11, 2016) "Mus musculus left right determination factor 1 (Leftyl), mRNAm," Accession Nos. NM 010094. National Center for Biotechnology Information. Accessible on the Internet at URL: http://www.ncbi.nlm.nih.gov/nuccore/NM_010094. [Last Accessed Sep. 16, 2016].

Han et al. (2010) "Tbx3 improves the germ-line competency of induced pluripotent stem cells," Nature. 463:1096-1100.

Hao et al. (2008) "Dorsomorphin, a Selective Small Molecule Inhibitor of BMP Signaling, Promotes Cardiomyogenesis in Embryonic Stem Cells," PLoS ONE 3(8):e2904. pp. 1-8.

Heng et al. (2010) "The nuclear receptor Nr5a2 can replace Oct4 in the reprogramming of murine somatic cells to pluripotent cells," Cell Stem Cell. 6:167-174.

Hosokawa et al. (Aug. 25, 2013) "[Regenerative medicine for diabetes using a progress iPS cells in the pathogenesis and treatment of diabetes]," Kidney and Dialysis. 75(2):268-273. 細川吉弥, 豊田太郎, 長船健二 (Aug. 25, 2013) "糖尿病の病態と治療における進歩 iPS 細胞を用いた糖尿病に対する再生医療," 腎と透析. 75(2):268-273.

Huangfu et al. (2008) "Induction of pluripotent stem cells by defined factors is greatly improved by small-molecule compounds" Nat. Biotechnol. 26:795-797.

Huangfu et al. (2008) "Induction of pluripotent stem cells from primary human fibroblasts with only Oct4 and Sox2," Nat. Biotechnol. 26:1269-1275.

Ichida et al. (2009) "A small-molecule inhibitor of tgf-Beta signaling replaces sox2 in reprogramming by inducing nanog," Cell Stem Cell. 5:491-503.

Ishizaki et al. (2000) "Pharmacological properties of Y-27632, a specific inhibitor of rho-associated kinases," Mol. Pharmacol. 57:976-983.

Jiang (2007) "In vitro derivation of functional insulin-producing cells from human embryonic stem cells," Cell Research. 17:333-344.

Judson et al. (2009) "Embryonic stem cell-specific microRNAs promote induced pluripotency," Nat. Biotech. 27:459-461.

Kagami et al. (2009) "[Natural compound with nuclear-receptor ligand binding activity]," Annual Report of Research Institute for Biological Function: Chubu University Research Institute for Biological Function. 9:55-61.—English machine translation of the abstract only.

Kanatsu-Shinohara et al. (2003) "Long-term proliferation in culture and germline transmission of mouse male germline stem cells," Biol. Reprod. 69:612-616.

Kanatsu-Shinohara et al. (2004) "Generation of pluripotent stem cells from neonatal mouse testis," Cell. 119:1001-1012.

Kawasaki et al. (2002) "Generation of dopaminergic neurons and pigmented epithelia from primate ES cells by stromal cell-derived inducing activity," Proc. Natl. Acad. Sci. USA. 99:1580-1585.

(56) References Cited

OTHER PUBLICATIONS

Kim et al. (2009) "Direct reprogramming of human neural stem cells by OCT4," Nature. 461:649-654.

Klimanskaya et al. (2006) "Human embryonic stem cell lines derived from single blastomeres," Nature. 444:481-485.

Kroon et al. (2008) "Pancreatic endoderm derived from human embryonic stem cells generates glucose-responsive insulin-secreting cells in vivo," Nature Biotechnology. 26(4):443-452.

Kunisada et al. (2012) "Small molecules induce efficient differentiation into insulin-producing cells from human nduced pluripotent stem cells," Stem Cell Res. 8(2):274-284.

Lindemann et al. (2003) "Interfering with TGFbeta-induced Smad3 nuclear accumulation differentially affects TGFbeta-dependent gene expression," Mol. Cancer. 2:20.

Lyssiotis et al. (2009) "Reprogramming of murine fibroblasts to induced pluripotent stem cells with chemical complementation of Klf4," Proc. Natl. Acad. Sci. USA. 106:8912-8917.

Maehr et al. (2009) "Generation of pluripotent stem cells from patients with type 1 diabetes," Proc. Natl. Acad. Sci. USA. 106(37):15768-15773.

Maekawa et al. (2011) "Direct reprogramming of somatic cells is promoted by maternal transcription factor Glis1," Nature. 474:225-229.

Mali et al. (2010) "Butyrate greatly enhances derivation of human induced pluripotent stem cells by promoting epigenetic remodeling and the expression of pluripotency-associated genes," Stem Cells. 28:713-720.

Marson et al. (2008) "Wnt signaling promotes reprogramming of somatic cells to pluripotency," Cell Stem Cell. 3:132-135.

Masanori et al. (2008) "[New Genetically Modified Stem Cell Strategy]," Experimental Medicine. 26(5): 41-46. 竹橋正則, 篠原美都, 篠原隆司 (2008) "精子幹細胞による新しい遺伝子改変ストラテジ —," 実験医学増刊. 26(5):41-46.—with English machine translation.

Matsui et al. (1992) "Derivation of pluripotential embryonic stem cells from murine primordial germ cells in culture," Cell. 70:841-847.

Nakagawa et al. (2008) "Generation of induced pluripotent stem cells without Myc from mouse and human fibroblasts," Nat. Biotechnol. 26:101-106.

Nakajima et al. (2003) "Effect of Wf-536, a novel ROCK inhibitor, against metastasis of B16 melanoma," Cancer Chemother. Pharmacol. 52(4):319-324.

Narumiya et al. (2000) "Use and properties of ROCK-specific inhibitor Y-27632," Methods Enzymol. 32:273-284.

Okita (2011) "A more efficient method to generate integration-free human iPS cells," Nat. Methods. 8:409-412.

Okita et al. (2008) "Generation of mouse induced pluripotent stem cells without viral vectors," Science. 322:949-953.

Osakada et al. (2008) "Toward the generation of rod and cone photoreceptors from mouse, monkey and human embryonic stem cells," Nat. Biotechnol. 26:215-224.

Resnik et al. (1992) "Long-term proliferation of mouse primordial germ cells in culture," Nature. 359:550-551.

Sasaki et al. (2002) "The novel and specific Rho-kinase inhibitor (S)-(+)-2-methyl-1-[(4-methyl-5-isoquinoline)sulfonyl]-homopiperazine as a probing molecule for Rho-kinase-involved pathway," Pharmacol. Ther. 93:225-232.

Shi et al. (2008) "A Combined Chemical and Genetic Approach for the Generation of Induced Pluripotent Stem Cells," Cell Stem Cell. 2:525-528.

Shi et al. (2008) "Induction of pluripotent stem cells from mouse embryonic fibroblasts by Oct4 and Klf4 with small-molecule compounds," Cell Stem Cell. 3:568-574.

Shim et al. (2007) "Directed differentiation of human embryonic stem cells towards a pancreatic cell fate," Diabetologia. 50:1228-1238.

Suemori et al. (2006) "Efficient establishment of human embryonic stem cell lines and long-term maintenance with stable karyotype by enzymatic bulk passage," Biochem. Biophys. Res. Commun. 345:926-932.

Suemori et al. (2001) "Establishment of embryonic stem cell lines from cynomolgus monkey blastocysts produced by IVF or ICSI," Dev. Dyn. 222:273-279.

Sun et al. (2009) "Feeder-free derivation of induced pluripotent stem cells from adult human adipose stem cells," Proc. Natl. Acad. Sci. USA. 106:15720-15725.

Takahashi et al. (2006) "Induction of pluripotent stem cells from mouse embryonic and adult fibroblast cultures by defined factors," Cell. 126:663-676.

Takahashi et al. (2007) "Induction of pluripotent stem cells from adult human fibroblasts by defined factors," Cell. 131:861-872.

INSULIN/Nuclei

INS: 4.9±1.2%
GCG: 1.9±0.3%

INS: 13.6±1.8%
GCG: 6.8±0.9%

Medium only

Sodium Cromoglicate (Fold)

METHOD FOR GENERATING PANCREATIC HORMONE-PRODUCING CELLS

RELATED APPLICATIONS

This application is a 35 U.S.C. §371 filing of International Application No. PCT/JP2014/070787, filed Aug. 6, 2014, which claims priority to Japanese Application No. 2013-164137, filed Aug. 7, 2013, each of which are incorporated herein by reference in their entireties.

TECHNICAL FIELD

The present invention relates to a method for generating pancreatic hormone-producing cells.

BACKGROUND ART

The pancreas functions as an exocrine ground that secretes digestive enzymes such as pancreas lipase, trypsin, elastase, pancreas amylase and also as an endocrine gland that secretes pancreatic hormones such as glucagon, insulin, somatostatin, and the pancreatic polypeptide (PP). Recently, it has been reported that ghrelin which is a gastric hormone is also secreted from the endocrine gland cells in the pancreas. The pancreatic hormones are produced by the cell mass in the pancreas called pancreatic islet which consists of four types of cells including α cells, β cells, δ cells and PP cells.

Insulin plays an important role in the control of the blood sugar level within a suitable amount. Insulin promotes the use of glucose, the synthesis of proteins and the production and storage of neutral fats and thereby lowers the blood sugar level. Glucagon also plays an important role together with insulin in the regulation of the glycometabolism. This hormone increases the blood sugar level through glycogenesis in the liver or gluconeogenesis. Somatostatin inhibits secretion of various hormones from pancreas. This hormone is activated via binding with somatostatin receptors. PP is a hormone secreted by Langerhans islets in response to food intake and is known as "satiety hormone". This hormone lowers food intake or weight increase. Ghrelin stimulates food intake and lowers oxidization of fats, and causes weight gain.

Diabetes is a disease that is developed due to a shortage or insufficient working of insulin. Once developed in a patient, the disease is hard to be cured completely. There are two major types of diabetes, type 1 diabetes that is also known as insulin-dependent diabetes and type 2 diabetes that is also known as insulin-independent diabetes.

Type 2 diabetes is a chronic disease that is developed where the body acquires insulin resistance. Type 2 diabetes is also known as a lifestyle-related disease developed due to bad lifestyle habitat including obesity or stress caused by overeating or lack of excise. Type 2 diabetes often occurs in the middle aged and elderly people. Many of diabetic patients have Type 2 diabetes.

Type 1 diabetes is caused by destruction of the beta cells or insulin producing cells by an autoimmune disease or viral infection. The insulin producing cells are destroyed and insulin is not secreted in the body. The patients with type 1 diabetes are administered with insulin as a symptomatic treatment. In addition, pancreas or islet transplantation has been applied so that the patient acquires the ability to control the blood sugar level automatically. The blood sugar level always fluctuates and the pancreas or islet transplantation could reduce the burden on the patients. This treatment could achieve the normal blood-sugar level in the patient. However, only insufficient number of pancreas and islets has been available for transplantation at present. The patient received transplantation must take an immunosuppressant for a lifetime and such a drug may cause infectious diseases or other side effects.

A treatment of type I diabetes including inducing insulin producing cells from the cells derived from the patient in vitro and transplanting the induced insulin producing cells to the patient's body has been proposed. For example, procedures to induce insulin producing cells in vitro from patient's own pancreas-tissue stem cells or pancreatic duct epithelium. Transplantation using insulin producing cells derived from patient's own cells is advantageous in safety and is free from the problem of immune rejection.

Methods for generating insulin producing cells known to the art include differentiating pluripotent stem cells such as embryonic stem (ES) cells or induced stem (iPS) cells, differentiating pancreas tissue stem cells, obtaining pancreatic duct epithelial cells from the body and differentiating the cells outside the body.

Methods for inducing insulin producing cells from pluripotent stem cells known to the art include inducing differentiation by using activin and retinoic acid (RA) (Patent Literature 1 and Non-Patent Literatures 1-5). In addition, insulin producing cells may also be induced by introducing PDX1 into pluripotent stem cells and culturing the same (Patent Literature 2 and 3), applying a combination of plurality of small molecule compounds to pluripotent stem cells to generate insulin-producing cells (patent literature 4 and non-patent literature 6).

CITED DOCUMENTS

Patent Literatures

[Patent Literature 1] JP2009-225661A
[Patent Literature 2] U.S. Pat. No. 7,534,608B
[Patent Literature 3] JP2006-075022A
[Patent Literature 4] WO2011/081222

Non-Patent Literatures

[Non-Patent Literature 1] E. Kroon et al., Nature Biotechnology (2008) Vol. 26, No. 4:443-452
[Non-Patent Literature 2] K. A. D'Amour et al., Nature Biotechnology (2006) Vol. 24, No. 11:1392-1401
[Non-Patent Literature 3] W. Jiang, Cell Research (2007) 17:333-344
[Non-Patent Literature 4] J. H. Shim et al., Diabetologia (2007) 50:1228-1238
[Non-Patent Literature 5] R. Maehra et al., PNAS (2009), vol. 106, No. 37:15768-15773
[Non-Patent Literature 6] Kunisada Y et al., Stem Cell Res. (2012) vol. 8, No. 2:274-284.

The above listed patent and non-patent literatures are herein incorporated by reference.

SUMMARY OF THE INVENTION

Technical Problem

An object of the present invention is to provide a method for generating pancreatic hormone-producing cells more efficiently. In particular, a method for generating a large number of pancreatic hormone-producing cells stably by inducing pluripotent stem cells into pancreatic hormone-producing cells.

Solution to Problem

The inventors have intensively studied on the above technical problem, and have found that in the method for generating insulin producing cells taught by Non-Patent Literature 6, the efficiency is augmented by adding sodium cromoglicate during the procedures to differentiate pluripotent stem cells into pancreatic hormone-producing cells, and completed the present invention.

The present invention provides the followings:
[1] A method for generating pancreatic hormone-producing cells, which comprises culturing pancreas progenitor cells in a medium comprising sodium cromoglicate.
[2] The method of [1], wherein the medium further comprises at least one agent selected from the group consisting of:
(a) at least one agent selected from the group consisting of an adenylate cyclase activator, a cAMP phosphodiesterase inhibitor and an cAMP analog;
(b) nicotinamide;
(c) a steroid; and
(d) a TGFβ inhibitor.
[3] The method of [1] or [2], wherein the medium further comprises:
(a) at least one agent selected from the group consisting of an adenylate cyclase activator, a cAMP phosphodiesterase inhibitor and an cAMP analog;
(b) nicotinamide;
(c) a steroid; and
(d) a TGFβ inhibitor.
[4] The method of [2] or [3], wherein the at least one agent selected from the group consisting of an adenylate cyclase activator, a cAMP phosphodiesterase inhibitor and an cAMP analog is forskolin.
[5] The method any one of [2] to [4], wherein the steroid is dexamethasone.
[6] The method any one of [2] to [4], wherein the TGFβ inhibitor is 2-(3-(6-Methylpyridin-2-yl)-1H-pyrazol-4-yl)-1, 5-naphthyridine.
[7] The method of any one of [1] to [6], wherein the pancreatic progenitor cells are the cells derived from a method comprising the following steps:
(1) culturing pluripotent stem cells in a medium comprising an activator of activin receptor-like kinase-4,7 and a GSK3 inhibitor, and
(2) culturing the cells obtained in step (1) in a medium comprising (a) a retinoic acid receptor agonist, (b) a BMP inhibitor and (c) a TGFβ inhibitor.
[8] The method of [7], wherein the activator of activin receptor-like kinase-4,7 is activin.
[9] The method of [7] or [8], wherein the GSK3 inhibitor is CHIR99021.
[10] The method of any one of [7] to [9], wherein the TGFβ inhibitor used in step (2) is SB431542.
[11] The method of any one of [7] to [10], wherein the BMP inhibitor is dorsomorphin.
[12] The method of any one of [1] to [11], wherein the pancreatic hormone-producing cells are selected from the group consisting of insulin producing cells, glucagon producing cells, somatostatin producing cells and pancreatic polypeptide producing cells.
[13] The method of [12], wherein the pancreatic hormone-producing cells are insulin producing cells and/or glucagon producing cells.
[14] The method of any one of [1] to [13], wherein the pancreatic progenitor cell are human cells.

Advantageous Effects of Invention

According to the present invention, pancreatic hormone-producing cells can efficiently be generated from pancreatic progenitor cells. The pancreatic hormone-producing cells generated by the method of the invention may be used for screening an agent which is useful for the treatment of a disease such as diabetes that is caused by abnormal pancreatic hormone-producing cells. The pancreatic hormone-producing cells generated by the method can be used as medical cell preparation for the treatment of the above discussed diseases.

DESCRIPTION OF EMBODIMENTS

Figure 1A:
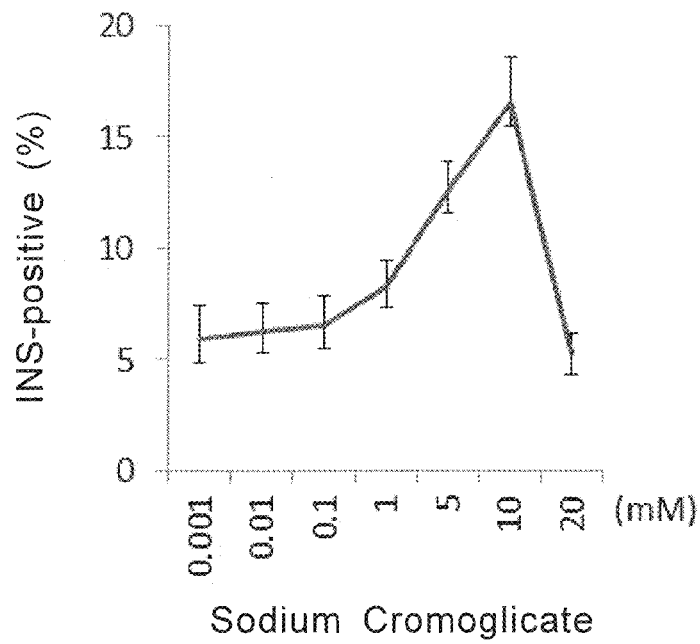
FIG. 1A is a graph showing the percentage of insulin positive cells in the cells differentiated from human iPS cell line 201B7 by culturing the cells in a medium added with various amount of sodium cromoglicate. Cells on day 23 or 12 days after the addition of sodium cromoglicate were analyzed.

The present invention provides a method for generating pancreatic hormone-producing cells, comprising the step of culturing pancreatic progenitor cells in a medium containing sodium cromoglicate.

The medium to be used for generating pancreatic hormone-producing cells may further comprise at least one agent selected from the group consisting of (a) at least one agent selected from the group consisting of an adenylate cyclase activator, a cAMP phosphodiesterase inhibitor and an cAMP analog, (b) nicotinamide, (c) steroid and at least one agent selected from the group consisting of (d) a TGFβ inhibitor, (f) KGF, (g) EGF and (h) a BMP inhibitor in addition to sodium cromoglicate. Preferably, the medium comprises (a) at least one agent selected from the group consisting of adenylate cyclase activator, cAMP phosphodiesterase inhibitor and a cAMP analog, (b) nicotinamide, (c) a steroid and (d) a TGFβ inhibitor.

The medium to be used for generating pancreatic hormone-producing cells may be prepared by adding the additives to a basal medium. Examples of basal media may include IMDM, Medium 199, Eagle's Minimum Essential Medium (EMEM), αMEM, Dulbecco's modified Eagle's Medium (DMEM), Improved MEM (invitrogen), Ham's F12, RPMI 1640, Fischer's medium, Neurobasal Medium (lifetechnologies), StemPro34 (invitrogen) and a mixture thereof. The basal medium may be serum-containing medium or a serum-free medium. The basal medium may comprise one or more serum substitutes for example, albumin, transferrin, Knockout Serum Replacement (KSR) which is a FBS substitute for culturing ES cells, N2 supplement (Invitrogen), B27 supplement (Invitrogen), a fatty acid, insulin, collagen precursor, a trace element, 2-mercaptethanol or 1-thiolglycerol. In addition, the basal medium may comprise one or more additional agents such as lipid, an amino acid, L-glutamine, Glutamax (Invitrogen), a non-essential amino acid, a vitamin, a growth factor, a small molecule compound, an antibiotic, an anti-oxidant, pyruvic acid, a buffering agent and an inorganic salt.

In the step of culturing the pancreatic progenitor cells in a medium comprising sodium cromoglicate, the cells may be subjected to suspension culture or adhesion culture. The medium used in this step may be an above discussed basal-medium added with sodium cromoglicate. Preferred basal medium may be Improved MEM containing B-27 supplements.

"Sodium cromoglicate" is sodium salt of 1,3-Bis(2-carboxychromon-5-yloxy)-2-hydroxypropane. This compound is available on the market from, for example, Sigma and Wako Pure Chemical Industries, Ltd. The concentration of sodium cromoglicate in the medium used in step 3 may usually be 0.001-100 mM, preferably, 0.01-50 mM and more preferably, 0.01-20 mM and especially, 10 mM.

In the present invention, "suspension culture" refers cell culture in the manner that the cells are not adhered to the inner wall of the culture plate. The culture plate to be used for suspension culture may be those having no treatment that improves the cell adherence to the inner wall the plate, such as culture plates having no extracellular matrix coatings, or those having artificial treatment to prevent cell adherence, such as culture plates having polyhydroxy methacrylic acid (poly-HEMA) coating.

The adherent culture may be conducted on feeder cells or in a culture plate with coatings. Feeder cells represent cells other than the objective cells to be cultured and used in order to support the growth of the objective cells in the culture. Examples of feeder cells may include fibroblast cells such as mouse embryonic fibroblast cells (MEF), mouse fibroblast cells (STO and SNL). Feeder cells may be mitotically inactivated by a known technique, for example, irradiation such as gamma-ray irradiation or by means of anticancer agent such as mitomycin C. Examples of coatings may include Matrigel™ (BD), collagen, gelatin, laminin, heparan sulfate proteoglycan, and entactin, a fragment thereof or a combination of thereof.

Examples of the agent selected from the group consisting of adenylate cyclase activator, cAMP phosphodiesterase inhibitor and an cAMP analog may be a compound that has the adenylate cyclase activity, a compound that has the cAMP phosphodiesterase inhibiting activity, and a compound that has both of the adenylate cyclase and the cAMP phosphodiesterase inhibiting activities. For example, the agent may be forskolin, di-butyl cAMP, PACAP27 (pituitary adenylate cyclase activating polypeptide 27), or IBMX (3-isobutyl-1-methylxanthine) and may preferably be forskolin.

When forskolin is employed as the agent selected from the group consisting of adenylate cyclase activators, cAMP phosphodiesterase inhibitors and cAMP analogs, the concentration of forskolin in the culture medium may be 0.1-50 µM in general and preferably 2-50 µM.

The concentration of nicotinamide in the medium may be 0.1-20 mM in general and preferably, 5-20 mM.

Examples of steroids may include dexamethasone, hydrocortisone, betamethasone and beclomethasone, and dexamethasone is preferably used. When dexamethasone is employed as the steroid, the concentration of dexamethasone in the culture medium may be 0.1-50 µM and preferably, 2-50 µM. When hydrocortisone is employed as the steroid, the concentration of hydrocortisone in the culture medium may be 0.1-100 µM and preferably, 1-50 µM. When betamethasone is employed as the steroid, the concentration of betamethasone in the culture medium may be 0.1-50 µM and preferably, 0.5-20 µM. When beclomethasone is employed as the steroid, the concentration of beclomethasone in the culture medium may be 0.1-50 µM and preferably, 0.2-20 µM.

A TGFβ inhibitor is an agent that inhibits signaling from binding of TGFβ and the receptor to SMAD. TGFβ inhibitors may be any agent that blocks binding of TGFβ to ALK family substances, or that inhibits phosphorylation of SMAD by ALK family substances. Examples of TGFβ inhibitors may include Lefty-1 (NCBI Accession Nos: NM_010094 (mouse) and NM_020997 (human)), SB431542 (4-[4-(1,3-benzodioxole-5-yl)-5-(2-pyridyl)-1H-imidazole2-yl]benzamide), and SB202190 (4-[4-(4-fluorophenyl)-5-(4-pyridyl)-1H-imidazole-2-yl]phenol) (R. K. Lindemann et al., Mol. Cancer, 2003, 2:20), SB505124 (GlaxoSmithKline), NPC30345, SD093, SD908, SD208 (Scios), LY2109761, LY364947, LY580276 (Lilly Research Laboratories), A-83-01 (WO 2009146408), ALK5 inhibitor II (2-[3-[6-methylpyridine2-yl]-1H-pyrazole-4-yl]-1,5-naphthyridine), TGFβRI kinase inhibitor VIII (6-[2-tert-butyl-5-[6-methyl-pyridine-2-yl]-1H-imidazole-4-yl]-quinoxaline) and derivatives thereof. The preferred TGFβ inhibitor to be added in the culture medium containing sodium cromoglicate is ALK5 inhibitor II. When ALK5 inhibitor II is employed as the TGFβ inhibitor, the concentration of ALK5 inhibitor II in the culture medium may be 0.5-100 µM, preferably 1-50 µM, and more preferably 1-10 µM.

"KGF" represents a protein called as Keratinocyte Growth Factor and is sometimes called as FGF-7. The concentration of KGF in the medium used in this invention may be 1 ng/ml-1 µg/ml, preferably 5 ng/ml-500 ng/ml, and more preferably 10 ng/ml-100 ng/ml.

"EGF" represents a protein called as Epidermal Growth Factor. The concentration of EGF in the medium used in this invention may be 1 ng/ml-1 µg/ml, preferably 5 ng/ml-500 ng/ml, and more preferably 10 ng/ml-100 ng/ml.

Examples of BMP inhibitors may include proteins such as Chordin, Noggin and Follistatin, dorsomorphin or 6-[4-(2-piperidine-1-yl-ethoxy)phenyl]-3-pyridine-4-yl-pyrazolo[1,5-a]pyrimidin) and derivatives thereof (P. B. Yu et al. (2007), Circulation, 116:II_60; P. B. Yu et al. (2008), Nat. Chem. Biol., 4:33-41; J. Hao et al. (2008), PLoS ONE, 3(8):e2904), and LDN-193189 or 4-(6-(4-(piperidine-1-yl)phenyl)pyrazolo[1,5-a]pyrimidin-3-yl)quinoline). Dorsomorphin (Sigma-Aldrich) and LDN-193189 (Stemgent) are available on the market.

The pancreatic progenitor cells may be cultured, for example, 4 days or more, 5 days or more, 6 days or more, 7 days or more, 8 days or more, 9 days or more, or 10 days or more. Preferably, the cells may be cultured 4 days or more and less than 20 days, and more preferably, 8 days or more and 16 days or less.

In the present invention, pancreatic progenitor cells represent the cells that can be induced into pancreatic hormone-producing cells. Pancreatic progenitor may be characterized as cells expressing PDX1 and not expressing insulin, glucagon, somatostatin, pancreatic polypeptide or ghrelin. In the present invention, the pancreatic progenitor cells may be isolated from the living body or obtained by differentiating pluripotent stem cells.

Pluripotent stem cells may be differentiated into pancreatic progenitor cells by a method that includes the following steps (1) and (2):
(1) culturing the pluripotent stem cells in a medium comprising an activator of activin receptor-like kinase-4,7 and a GSK3 inhibitor, and
(2) culturing the cells obtained in step (1) in a medium comprising at least one agent selected from the group consisting of (a) a retinoic acid receptor agonist, (b) a BMP inhibitor and (c) a TGFβ inhibitor.

Accordingly, the present invention also provides a method for generating pancreatic hormone-producing cells from pluripotent stem cells, comprising the following steps (1)-(3):
(1) culturing the pluripotent stem cells in a medium comprising an activator of activin receptor-like kinase-4,7 and a GSK3 inhibitor;
(2) culturing the cells obtained in step (1) in a medium comprising at least of agent selected from the group consisting of (a) a retinoic acid receptor agonist, (b) a BMP inhibitor, and (c) a TGFβ inhibitor;
(3) culturing the cells obtained in step (2) in a medium comprising sodium cromoglicate.

Pluripotent stem cells refer stem cells that have pluripotency and growth ability by self-renewal, i.e. those having the potential to differentiate into many types of cells in the body. Examples of pluripotent stem cells may include embryonic stem cells (ES cells), nuclear transfer embryonic stem cells (ntES cells), germline stem cells (GS cells), embryonic germ cells (EG cells), induced pluripotent stem cells (iPS cells), Muse cells that are pluripotent cells derived from cultured fibroblast cells or bone marrow stem cells. iPS cells and Muse cells are preferable in view of the fact that those pluripotent stem cells can be obtained by not destroying the embryos. The pluripotent stem cells are preferably those derived from mammal and more preferably, are human pluripotent stem cells.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292: 154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165). The contents of the documents cited in this paragraph are herein incorporated by reference.

ES cells can be established by removing the inner cell mass from the blastocyst of a fertilized egg of the subject animal, followed by culturing the inner cell mass on fibroblasts as feeders. The cells can be maintained by subculturing using a medium supplemented with substances such as leukemia inhibitory factor (LIF) and basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99: 1580-1585; and Klimanskaya I, et al. (2006), Nature. 444:481-485. The contents of the documents cited in this paragraph are herein incorporated by reference.

Human ES cells may be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 5% $CO_2$/95% air (O. Fumitaka et al. (2008), Nat. Biotechnol., 26:215-224). Further, ES cells need to be subcultured every 3 to 4 days, and the subculture may be carried out using 0.25% trypsin and 0.1 mg/ml collagenase IV in PBS supplemented with 1 mM $CaCl_2$ and 20% KSR.

Selection of ES cells may generally be carried out by the Real-Time PCR method using as an index expression of a gene marker such as alkaline phosphatase, Oct-3/4 and Nanog. In particular, for selection of human ES cells, expression of a gene marker such as OCT-3/4, NANOG and ECAD may be used as an index (E. Kroon et al. (2008), Nat. Biotechnol., 26:443-452). The contents of the documents cited in this paragraph are herein incorporated by reference.

Human ES cell lines are available from various research institutes. For example, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and are the origin for spermatogenesis. Similarly to ES cells, these cells may be differentiated into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119: 1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)). The contents of the documents cited in this paragraph are herein incorporated by reference.

(C) Embryonic Germ Cells

Embryonic germ cells are established from fetal primordial germ cells and have pluripotency similar to that of ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551). The contents of the documents cited in this paragraph are herein incorporated by reference.

(D) Induced Pluripotent Stem Cells

Induced pluripotent stem (iPS) cells can be prepared by introducing specific reprogramming factors to somatic cells. iPS cells are somatic cell-derived artificial stem cells having properties almost equivalent to those of ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106(2008); and WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbxl5, ERas, ECAT15-2, Tell, beta-catenin, Lin28b, Sall1, Sall4, Esrrb, Nr5a2, Tbx3 and Glis1, and these reprogramming factors may be used either individually or in combination. Examples of the combination of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26: 1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al. (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6: 167-74; Han J, et al. (2010), Nature. 463:1096-100; Mali P, et al. (2010), Stem Cells. 28:713-720, and Maekawa M, et al. (2011), Nature. 474: 225-9. The contents of the documents cited in this paragraph are herein incorporated by reference.

The reprogramming factors may be contacted with or introduced into the somatic cells by a known procedure suitable for the form of the factor to be used.

In cases where the reprogramming factors are in the form of protein, the reprogramming factors may be introduced into somatic cells by a method such as lipofection, fusion with a cell-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vector may contain a regulatory sequence(s) such as a promoter, enhancer, ribosome binding sequence, terminator and/or polyadenylation site to enable expression of the nuclear reprogramming factors; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG. Further, in order to remove, after introduction of the gene into the somatic cells and expression of the same, the genes encoding the reprogramming factors, or both the promoter(s) and the genes encoding the reprogramming factors linked thereto, the vector may have LoxP sequences upstream and downstream of these sequences. The contents of the documents cited in this paragraph are herein incorporated by reference.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L, (2010) Cell Stem Cell. 7:618-630). The documents cited in this paragraph are herein incorporated by reference.

Examples of the medium for induction of the iPS cells include DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the method to induce iPS cells include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing ES-like colonies to appear about 30 to about 45 days after the contact, or later.

Alternatively, the cells may be contacted with the reprogramming factors and cultured at 37° C. in the presence of 5% $CO_2$ on feeder cells (e.g., mitomycin C-treated STO cells or SNL cells) in DMEM medium supplemented with 10% FBS (this medium may further contain LIF, penicillin/streptomycin, puromycin, L-glutamine, non-essential amino acids, β-mercaptoethanol and the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349), Laminin-10 (US2008/0213885) or its fragment (WO2011/043405) or Matrigel (BD)) is used instead. The documents cited in this paragraph are herein incorporated by reference.

Other examples include a method wherein the iPS cells are established using a serum-free medium (Sun N, et al. (2009), Proc Natl Acad Sci USA. 106: 15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO2010/013845). The contents of the documents cited in this paragraph are herein incorporated by reference.

Examples of factors used for enhancing the establishment efficiency may include histone deacetylase (HDAC) inhibitors[e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (for example, Bayk8644), butyric acid, TGFβ inhibitor or ALK5 inhibitor (e.g., LY364947, SB431542, 616453 and A-83-01), p53 inhibitor (for example, siRNA and shRNA against p53), ARID3A inhibitor (e.g., siRNA and shRNA against ARID3A), miRNA such as miR-291-3p, miR-294, miR-295, mir-302 and the like, Wnt Signaling (for example, soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. Upon establishing iPS cells, a medium added with the factor for enhancing the establishment efficiency may be used.

During the culture, the medium is replaced with the fresh medium once every day from Day 2 of the culture. The number of somatic cells used for nuclear reprogramming is not restricted, and usually within the range of about $5 \times 10^3$ to about $5 \times 10^6$ cells per 100-$cm^2$ area on the culture plate.

iPS cells may be selected based on the shape of each formed colony. In cases where a drug resistance gene is introduced as a marker gene such that the drug resistance gene is expressed in conjunction with a gene that is expressed when a somatic cell was reprogrammed (e.g., Oct3/4 or Nanog), the established iPS cells can be selected by culturing the cells in a medium containing the corresponding drug (selection medium). Further, iPS cells can be selected by observation under a fluorescence microscope in cases where a gene of a fluorescent protein is introduced as a marker gene. iPS cells can also be selected by adding a luminescent substrate in cases where a gene of a luminescent enzyme is introduced as a marker gene.

The term "somatic cells" used in the specification and claims means any animal cells (preferably cells of a mammal including human) excluding pluripotent cells such as sperms, spermatocytes, eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Specific examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

(E) ES Cells Derived from Cloned Embryo Obtained by Nuclear Transfer ntES cells are ES cells derived from a cloned embryo prepared by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for several hours. The documents cited in this paragraph are herein incorporated by reference.

(F) Multilineage-Differentiating Stress Enduring Cell (Muse Cell)

Muse cell is a pluripotent stem cell produced by the method described in WO2011/007900. In more detail, it is a cell having pluripotency, which is obtained by subjecting a fibroblast or a bone marrow stromal cell to a trypsin treatment for a long time, preferably 8 hr or 16 hr, and thereafter culturing the cells in a suspended state, and positive for SSEA-3 and CD105.

Pancreatic hormone-producing cells represent cells that have an ability to produce a pancreatic hormone. Examples of pancreatic hormones may include insulin, glucagon, somatostatin, pancreatic polypeptide, and ghrelin. Pancreatic hormone-producing cells are those having an ability to produce a pancreatic hormone and are not necessary always produce the cells. There is no limitation regarding the amount of the pancreatic hormone produced by the cell in order to a cell is defined as a pancreatic hormone-producing cell. Examples of pancreatic hormone-producing cells may include insulin producing cells, glucagon producing cells, somatostatin producing cells and pancreatic peptide producing cells.

Pancreatic hormone-producing cells may be induced from pluripotent stem cells by a method comprising the following steps 1 and 2.

<Step 1>

Step of culturing the pluripotent stem cell in a medium comprising an activator of activin receptor-like kinase-4,7, and a GSK3 inhibitor.

Pluripotent stem cells are in general grown in adherent culture. In step 1, the pluripotent stem cells may be dissociated by any known procedure and cultured in suspension culture or in adherent culture with feeder cells or in a culture plate with a coating.

The cells may be mechanically dissociated, or may be dissociated using a dissociation solution having protease and collagenase activities (e.g., Accutase™ or Accumax™), or a dissociation solution having only collagenase activity. Preferably, colonies of pluripotent stem cells may be dissociated by using a dissociation solution having protease and collagenase activities, especially Accumax™ and then by using mechanical power to give single cell suspension. The human pluripotent stem cells to be used in Step 1 are preferably that are grown to 80% or more confluence in the culture plate.

Pluripotent stem cells may be cultured in adherent culture on feeder cells or in a culture plate with a coating. Feeder cells are cells which are used to support the growth of the other cells in culture. Examples of feeder cells may include fibroblast cells such as murine embryonic fibroblasts (MEF) and mouse fibroblast cells such as STO cells and SNL cells. Feeder cells are preferably inactivated by irradiation such as gamma irradiation or exposing the cells to anti-cancer drug such as Mitomycin C. Culture plate to be used in the adherent culture may be coated with a coating agent. Examples of coating agents may include Matrigel (BD), collagen, gelatin, laminin, heparan sulfate proteoglycan and entactin, and a combination thereof.

Step 1 may be started by changing the culture medium for maintenance of the pluripotent stem cells with the medium for this step, or transferring the pluripotent stem cells dissociated from the original culture to a culture plate for adherent culture or suspension culture containing the medium for this step. The culture medium used in Step 1 may be prepared by adding an activator of activin receptor-like kinase-4,7, and a GSK inhibitor to an above explained basal medium. The basal medium preferably used in step 1 may be RPMI 1640 supplemented with B27 and RPMI 1640 supplemented with serum.

The activator of activin receptor-like kinase-4,7 is an agent that can activate ALK-4 and/or ALK-7. Examples of the agents may include activin, Nodal and Myostatin, and preferably, activin may be used. Activin A, activin B, activin C, activin D and activin AB are known. Any of activins A, B, C, D and AB may be used, and activin A is preferably used in Step 1. In addition the activin may be that derived from a mammal such as human or mice. Activin derived from an animal species that is equal to the species from which the pluripotent stem cells used as the starting material are derived. For example, in the case human pluripotent stem cells are used as starting material, activin derived from human may preferably be used. Activins are commercially available on the market.

The concentration of activin in the medium used in step 1 may be 0.1-200 ng/ml, preferably 5-150 ng/ml and more preferably, 10-100 ng/ml.

"GSK3 inhibitor" is defined as a substance that inhibits the kinase activity of GSK-3β, for example, a substance that inhibits phosphorylation of β-catenin. Many GSK3 inhibitors have been known. Examples of GSK3 inhibitors may include an indirubin derivative such as "BIO" or GSK-3β inhibitor IX (6-bromoindirubin-3'-oxime), maleimide derivatives such as SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrol-2,5-dione), a phenyl-α-bromomethyl-ketone such as GSK-3β inhibitor VII (4-dibromoacetophenone), a cell membrane-permeable type phosphorylated peptide such as L803-3ts (GSK-3β peptide inhibitor; Myr-N-GKEAPPAPPQSpP-NH2) and CHIR99021 (6-[[2-[[4-(2,4-dichloro0phenyl)-5-(4-methyl1H-imidazole2-yl)-2-pyrimidinyl]amino]ethyl]amino]nicotinonitrile) which has a high selectivity. Those compounds are easily available on the market from, for example, Calibiochem and Biomol. Those compounds may be obtained from the other companies or prepared. The preferred GSK-3β inhibitor used in step 1 may be CHIR99021.

When CHIR99021 is used in step 1, the concentration of the compound in the medium may be 0.01 μM-100 μM, preferably 0.1 μM-10 μM, and more preferably, 1 μM-5 μM.

In step 1, the medium may further comprise a ROCK inhibitor. ROCK inhibitors that may be used in this step are not specifically limited as long as the agent suppresses the Rho-kinase (ROCK) activity. Examples of ROCK inhibitors may include Y-27632 (Ishizaki et al., Mol. Pharmacol. 57, 976-983 (2000); Narumiya et al., Methods Enzymol. 325, 273-284 (2000)), Fasudil/HA1077 (Uenata et al., Nature 389: 990-994 (1997)), H-1152 (Sasaki et al., Pharmacol. Ther. 93: 225-232 (2002)), Wf-536 (Nakajima et al., Cancer Chemother Pharmacol. 52(4): 319-324 (2003)) and derivatives thereof. In addition, antisense nucleic acid against ROCK, RNA interfering nucleic acid such as siRNA, dominant negative mutant of ROCK and an expression vector thereof may also be used as a ROCK inhibitor. Further, any known small molecule compound that has been known to be a ROCK inhibitor may also be used in step 1. See US2005/0209261A, US2005/0192304A, US2004/0014755A, US2004/0002508A, US2004/0002507A, US2003/0125344A, US2003/0087919A, WO2003/062227A, WO2003/059913A, WO2003/062225A, WO2002/076976A and WO2004/039796A. In this invention, one, two or more ROCK inhibitors may be used. The preferred ROCK inhibitor used in step 1 may be Y-27632. The contents of the documents cited in this paragraph are herein incorporated by reference.

When Y-27632 is used in step 1, the concentration of the compound in the medium may be 0.1 μM-100 μM, preferably 1 μM-50 μM, and more preferably, 5 μM-20 μM. The ROCK inhibitor is added in order to avoid cell death at the beginning of the culture, in more detail, to avoid cell death when dissociating the pluripotent cell culture from the culture plate. Accordingly, the ROCK inhibitor is not necessary present throughout the culture but the compound should be present 1-2 days at the beginning of step 1.

The culturing period in step 1 may be, for example 3 days or more, 4 days or more, 5 days or more, 6 days or more, 7 days or more, 8 days or more, 9 days or more, or 10 days or more. There is no upper limit for the period of culturing the cells in step 1 and there is no disadvantage caused by culturing the cells longer. For example, the cells may be cultured for 5-12 days and preferably, for 5 days.

<Step 2>

Step culturing the cells in a medium added with an agent selected from the group consisting of retinoic acid receptor agonist, a BMP inhibitor and a TGFβ inhibitor.

Step 1 is followed by step 2. In step 2, the cells obtained in step 1 may be transferred to another culture plate containing the culture medium for step 2. Alternatively, the cells may be cultured in the same culture plate as step 1 and the medium used in step 1 may be changed to the medium for step 2. In step 2, the cells may be cultured in suspension culture or adherent culture. When the cells are cultured in adherent culture in step 1 and then, are transferred to another culture plate, the cells obtained in step 1 may be dissociated from the culture plate by any of known procedures. The medium for step 2 may be prepared by adding a substance selected from the group consisting of a retinoic acid receptor agonist, a BMP inhibitor and a TGFβ inhibitor to the above discussed basal medium. Preferred basal medium is Improved MEM medium supplemented with B-27 supplement.

Retinoic acid receptor (RAR) agonist used in step 2 may be naturally occurred retinoid, chemically synthesized retinoid, a retinoic acid receptor agonist that does not have the retinoid structure, or a naturally occurred substance that has the retinoic acid receptor agonist activity. Examples of naturally occurred retinoid having the retinoic acid agonist activity may include retinoic acid such as all-trans retinoic acid (all trans RA) and 9-cis-retinoic acid (9-cisRA). Chemically synthesized retinoid is known to the art (for example, U.S. Pat. Nos. 5,234,926 and 4,326,055). Examples of retinoic acid receptor agonists that do not have the retinoid structure may include Am80, AM580, TTNPB, and AC55649. Examples of naturally occurred substances that have the retinoic acid receptor agonist activity may include magnolol and honokiol (Annual Report of Research Institute for biological Function 9:55-61, 2009). The RAR agonist used in step 2 may preferably be retinoic acid, AM580 (4-[[5,6,7,8-tetrahydro-5,5,8,8-tetramethyl-2-naphthalenyl]carboxyamide]benzoic acid), TTNPB (4-[[E]-2-[5,6,7,8-tetrahydro-5,5,8,8-tetramethyl-2-naphthalenyl]-1-propenyl]benzoic acid), and AC55649 (4'-octyl-[1,1'-biphenyl]-4-carboxylic acid) and more preferably, retinoic acid.

When retinoic acid is used as an RAR agonist in step 2, the concentration of the compound in the medium may be 0.1 μM-100 μM and preferably 0.5 μM-10 μM. When TTNPB is used as an RAR agonist, the concentration of the compound in the medium may be 0.02 μM-20 μM and preferably 0.05 μM-10 μM. When AM580 is used as an RAR agonist, the concentration of the compound in the medium may be 0.02 μM-20 μM and preferably 0.05 μM-10 μM. When AC55649 is used as an RAR agonist, the concentration of the compound in the medium may be 0.02 μM-20 μM and preferably 0.1 μM-10 μM.

The above discussed BMP inhibitors may also be used in step 2. Dorsomorphin may preferably be used in step 2.

When dorsomorphin is used as a BMP inhibitor in step 2, the concentration of the compound in the medium may be 0.01 μM-100 μM, preferably 0.1 μM-10 μM and more preferably 0.5 μM-5 μM.

The above discussed TGFβ inhibitors may also be used in step 2. SB431542 may preferably be used in step 2.

When SB431542 is used as a TGFβ inhibitor in step 2, the concentration of the compound in the medium may be 0.01 μM-100 μM, preferably 0.1 μM-50 μM and more preferably 1 μM-20 μM.

In step 2, KGF may be used instead of TGFβ inhibitor. When KGF is used in step 2, the concentration of the compound in the medium may be 1 ng/ml-1 μg/ml, preferably 5 ng/ml-500 ng/ml and more preferably, 10 ng/ml-100 ng/ml.

The culturing period in step 2 may be, for example, 3 days or more, 4 days or more, 5 days or more, 6 days or more, 7 days or more, 8 days or more, 9 days or more, or 10 days or more. There is no upper limit for the period of culturing the cells in step 2 and there is no disadvantage caused by culturing the cells longer. For example, the cells may be cultured for 6-12 days and preferably, for 6 days.

The pancreatic hormone-producing cells obtained by the present invention may be selected from the group consisting, for example, insulin producing cells, glucagon producing cells, somatostatin producing cells and pancreatic peptide producing cells. The type of the obtained cells may be identified by determining the type of the pancreatic hormone produced by the cell. The pancreatic hormone-producing cells may be provided as a cell population containing cells other than pancreatic hormone-producing cells in addition to the desired cells. Alternatively, the pancreatic hormone-producing cells may be purified by precipitating the cells using an antibody which specifically binds to a G6PC2-encoded Cell Surface Tag (WO2010/037784, contents of this document is herein incorporated by reference), by means of magnetic isolation using magnetic beads (for example, MACS), by labelling the cells with fluorescent labels and sorting the cells using cell sorter, or by using a substrate attached with an antibody such as a cell concentrating column.

Expression of a pancreatic hormone may be identified by the expression of the pancreatic hormone protein or polynucleotide coding for the pancreatic hormone. Secretion of a pancreatic hormone from the cells may be determined by any know procedure, such as western blotting, ELISA or the like by using an antibody which recognizes the pancreatic hormone protein.

The amount of the pancreatic hormone expressed in the cells may be determined by measuring the amount of the polynucleotide expression such as mRNA which encodes the pancreatic hormone protein in the cells. The amount of mRNA may be measured by any known procedure such as northern hybridization, SI mapping, PCR, quantitative RT-PCR, DNA tip or DNA-Allay method, or the like.

The present invention further provides a method for screening a substance that improves the efficacy for inducing pancreatic hormone-producing cells. The method comprises the steps as follows:
(1) culturing the pancreatic progenitor cells in a medium comprising sodium cromoglicate and a test substance,
(2) determining the amount of pancreatic hormone expressed in the cells obtained in the above step (1) and that in the cells obtained in the same manner as step (1) except for the culture medium does not contain the test substance,
(3) comparing the amount of pancreatic hormone expression in the cells obtained by culturing the cells in the presence of the test substance with the amount in the cells obtained without the test substance. When the amount of the pancreatic hormone expression in the cells obtained by culturing in the presence of the test substance is higher than that in the cells obtained by culturing the cells in the absence of the substance, the test substance is selected as a substance that improve the efficiency for inducing pancreatic hormone-producing cells.

In step (1), the culture medium may further comprise at least one agent selected from the group consisting of: (a) at least one agent selected from the group consisting of an adenylate cyclase activator, a cAMP phosphodiesterase inhibitor, and an cAMP analog, (b) nicotinamide, (c) a steroid and (d) a TGFβ inhibitor. Preferably, the cells in step (1) may be cultured in a medium that may further comprise at least one (a) at least one substance selected from the group consisting of an adenylate cyclase activator, a cAMP phosphodiesterase inhibitor, and an cAMP analog, (b) nicotinamide, (c) a steroid and (d) a TGFβ inhibitor.

Test substances may be peptides, proteins, antibodies, non-peptide compounds, synthesized compound, fermented products, cell extracts, plant extracts, animal tissue extracts and plasma. The test compound may be in a form of salt. The salt may be a salt with a pharmaceutically acceptable acid such as inorganic and organic salts, a salt with a base such as an alkaline metal salt, alkaline earth metal salt and aluminum salt. Examples of inorganic acids may include hydrochloric acid, phosphoric acid, hydrobromic acid, and sulfuric acid. Examples of organic acids may include acetic acid, formic acid, propionic acid, fumaric acid, maleic acid, succinic acid, tartaric acid, citric acid, malic acid, oxalic acid, benzoic acid, methanesulphonic acid, and benzene sulphonic acid. Examples of salts may comprise sodium salt, potassium salt, calcium salt, magnesium salt, barium salt and aluminum salt.

According to the present invention, a method for screening a substance that promotes a pancreatic hormone secretion. The method includes the following steps:
(1) culturing the pancreatic hormone-producing cells obtained by the present invention in a medium containing a test substance,
(2) determining the amount of pancreatic hormone expressed in the cells obtained in the above step (1) and that in the cells obtained in the same manner as step (1) except for the culture medium does not contain the test substance,
(3) comparing the amount of pancreatic hormone expression in the cells obtained by culturing the cells in the presence of the test substance with the amount in the cells obtained without the test substance. When the amount of the expression in the cells obtained by culturing in the presence of the test substance is higher than that in the cells obtained by culturing the cells in the absence of the substance, the test substance is selected as a substance that promotes the secretion of pancreatic hormone.

In the method for screening a substance that promotes the secretion of a pancreatic hormone, test substances and the procedures to be used for determining the amount of expression may be those described as above or others.

The pancreatic hormone-producing cells obtained by the present invention may be used for the treatment of a pancreatic disease by implanting the cells to the patient. The present invention further provides a composition for the treatment of a pancreatic disease that comprises the pancreatic hormone-producing cells obtained by the present invention. The cells may be treated so that the cell growth is suppressed such as irradiation or the treatment with mitomycin C before the implantation.

Treatment of a pancreatic disease may be conducted by implanting the pancreatic hormone-producing cell-suspension in saline or the like directly to pancreas, mesentery, spleen or liver. Cells may be implanted with a scaffold material such as polyethylene glycol, gelatin or collagen. The number of the cells administered to a patient may be, for example, $1\times10^8$-$1\times10^{10}$ cells/body, preferably $5\times10^8$-$1\times10^{10}$ cells/body and more preferably $1\times10^9$-$1\times10^{10}$ cells/body.

iPS cells are preferable starting material for generating pancreatic hormone-producing cells for implantation. It is preferable to use iPS cells induced from somatic cells derived from an individual whose HLA genes are same or substantially same as that of the subject who will receive the implantation in order to avoid rejection upon implantation. In this context, "substantially same" means the HLAs of the donor of the somatic cells from which iPS cells were induced match to those of the recipient to the extent that the immune reaction of the recipient against the implanted cells can be suppressed by using an immunosuppressant. For example, iPS cells may be induced from somatic cells derived from a donor whose three gene locus, HLA-A, HLA-B and HLA-DR, or four gene locus further including HLA-C are identical to those of the patient to whom the cells are implanted.

EXAMPLES

The present invention will be explained in more detail referring to the examples shown below. The scope of the present invention will not be limited to those examples.

Example 1

Examination of Effects of Sodium Cromoglicate

Human ES cell line KhES3 was obtained from Kyoto University and maintained in the manner as shown in H. Suemori et al. (2006), Biochem. Biophys. Res. Commun., 345:926-932, the contents of this document is herein incorporated by reference. The cells of KhES3 were differentiated into insulin producing cells according to the steps shown below. The colonies of the human ES cell line grown to approximately 70% confluent in the culture plate were dissociated from the plate by using CTK solution (Reprocell). The dissociated colonies were then divided into single cells using Accutase™ and seeded in 24 well plates (Greiner) at $2.0 \times 10^5$/well.

<Step 1>

The cells were cultured in RPMI medium containing 2% FBS added with activin A (100 ng/ml) and CHIR99021 (3 µM) for 5 days.

During this period, the medium was changed with the same fresh medium on the third and the fourth days.

<Step 2>

The cells obtained in Step 1 were cultured in improved MEM Zinc Option medium containing 1% B-27 (Invitrogen Corp.) comprising dorsomorphin (1 µM), retinoic acid (2 µM), and SB431542 (10 µM) for 6 days. During this period, the medium was changed with the same fresh medium every two days.

<Step 3>

The cells obtained in Step 2 were cultured in improved MEM Zinc Option medium containing 1% B-27 (Invitrogen Corp.) added with forskolin (10 µM), nicotinamide (10 mM), dexamethasone (10 µM), ALK5 inhibitor II ((2-(3-(6-Methylpyridin-2-yl)-1H-pyrazol-4-yl)-1,5-naphthyridine)) (5 µM) and sodium cromoglicate (0.001 mM, 0.01 mM, 0.1 mM, 1 mM, 5 mM, 10 mM or 20 mM) for more 12 days. During this period, the medium was changed with the same fresh medium every four days.

The obtained cells were treated by using BD Cytofix/Cytoperm™ Kit and then, stained with polyclonal guinea-pig anti Swine insulin antibody/anti-serum (DAKO) and analyzed using flow cytometry to determine the number of insulin producing cells. The addition of sodium cromoglicate in the culture medium increased the ratio of insulin positive cells in a concentration dependent manner.

Example 2

Example with an iPS Cell Line

Human iPS cell line 201B7 (this cell line can be obtained from Center for iPS Cell Research And Application, Kyoto University, Takahashi K et al, Cell. 2007 131:861-72., the contents of this document is incorporated herein by reference) was used. The iPS cells were differentiated into insulin producing cells by using the following steps. The colonies of the iPS cell line were grown to 70% confluent in the culture plate and dissociated from the plate by using CTK solution (Reprocell). The dissociated colonies were then divided into single cells using Accutase™ and seeded in 24 well plates (Greiner) at $2.0 \times 10^5$/well.

<Step 1>

The cells were cultured in RPMI medium containing 2% FBS added with activin A (100 ng/ml) and CHIR99021 (3 µM) for 5 days. During this period, the medium was changed with the same fresh medium on the third and the fourth days.

<Step 2>

The cells obtained in Step 1 were cultured in improved MEM Zinc Option medium containing 1% B-27 (Invitrogen Corp.) added with dorsomorphin (1 µM), retinoic acid (2 µM), and SB431542 (10 µM) for 6 days. During this period, the medium was changed with the same fresh medium every two days.

<Step 3>

The cells obtained in Step 2 were cultured in improved MEM Zinc Option medium containing 1% B-27 (Invitrogen Corp.) added with forskolin (10 µM), nicotinamide (10 mM), dexamethasone (10 µM), ALK5 inhibitor II ((2-(3-(6-methylpyridin-2-yl)-1H-pyrazol-4-yl)-1,5-naphthyridine)) (5 µM) and sodium cromoglicate (0.001 mM, 0.01 mM, 0.1 mM, 1 mM, 5 mM, 10 mM or 20 mM) for more 12 days. During this period, the medium was changed with the same fresh medium every four days.

The obtained cells analyzed using flow cytometry to determine the number of insulin producing cells in the same manner as Example 1. The addition of 1 mM or more sodium cromoglicate in the culture medium increased the ratio of insulin positive cells and the maximum insulin positive cell-ratio was obtained when 10 mM sodium cromoglicate was added (FIG. 1A).

Figure 1B:
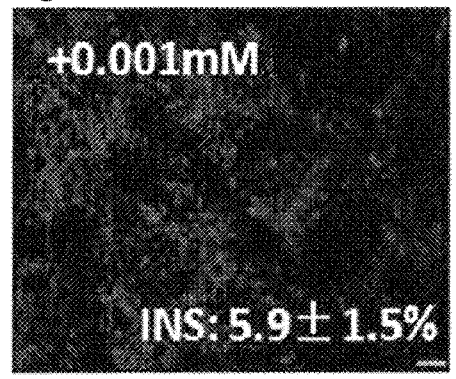
FIG. 1B represents immunostaining with anti-insulin antibody of the cells differentiated by adding 0.001 mM or 10 mM of sodium cromoglicate.
Figure 1B:
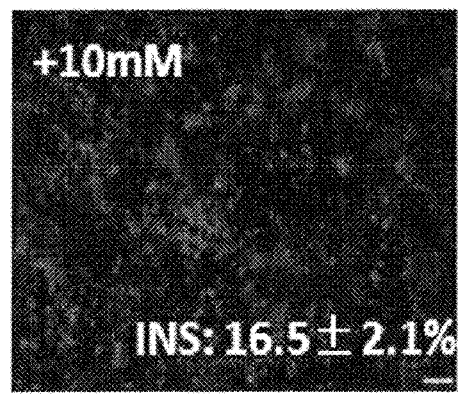
Figure 1C:
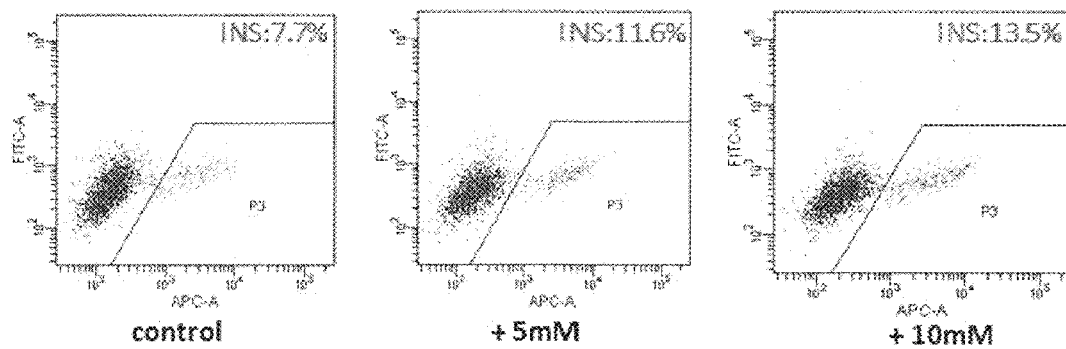
FIG. 1C represents flow cytometry analysis of the cells on day 23 differentiated from human iPS cell line 201B7 by using various concentration of sodium cromoglicate. The upper views represent insulin positive cells and the lower views represent c-peptide positive cells.

Insulin production was confirmed by immune staining of the cells (FIG. 1B). Further, cells were stained with anti-human C-peptide antibody (Peninsula Laboratories LLC.) and analyzed by flow cytometry to see the production of C-peptide which is obtained by processing of pro-insulin. The production of C-peptide was increased by addition of sodium cromoglicate in a dose dependent manner (FIG. 1C).

Example 3

Examination of Various Conditions

Three iPS cell lines, 418C1 and 409B2 (Okita K, et al, Nat Methods. 2011 8:409-412) and 201B7, all of which were generated from fibroblast cells, can be obtained from Center for iPS Cell Research and Application, Kyoto University. The iPS cell lines obtained from Kyoto University were differentiated into insulin positive cells by subjecting the cells to the same steps as those in Examples 1 and 2 with the exception that the concentration of sodium cromoglicate in the culture medium used in step 3 was 10 mM.

Figure 2A:
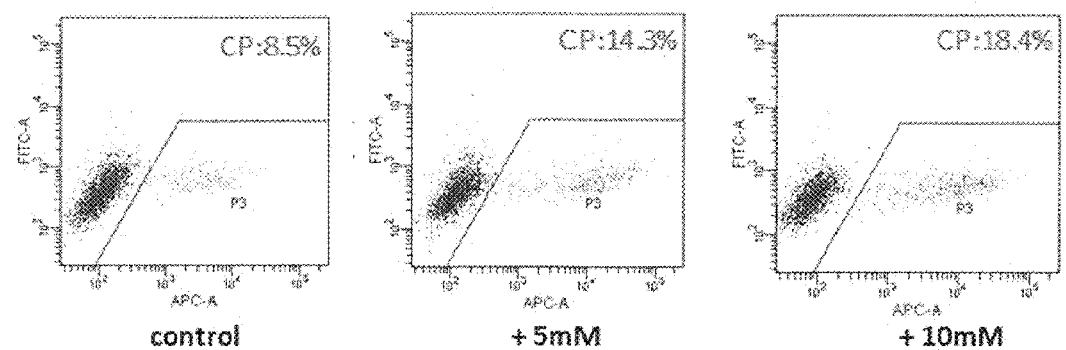
FIG. 2A Differentiation of multiple iPS cell lines (409B2, 418C1 and 201B7) into insulin positive cells. The iPS cells were treated with or without (control) 10 mM sodium cromoglicate. The percentages of insulin positive cells on day 23 are shown.
Figure 2A:
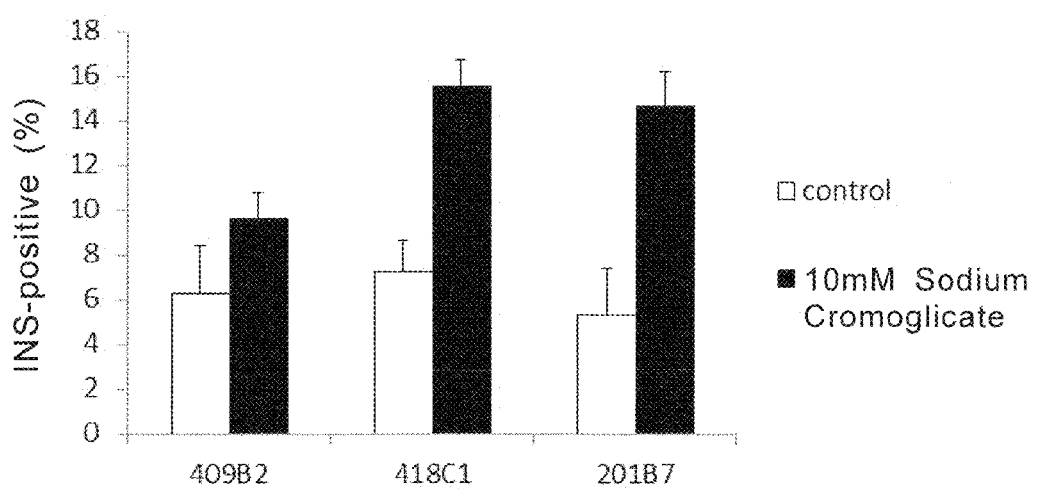

Results showed that all three iPS cell lines were differentiated into insulin positive cells and the ratio of insulin positive cells were increased by the addition of sodium cromoglicate in step 3 (FIG. 2A).

Figure 2B:
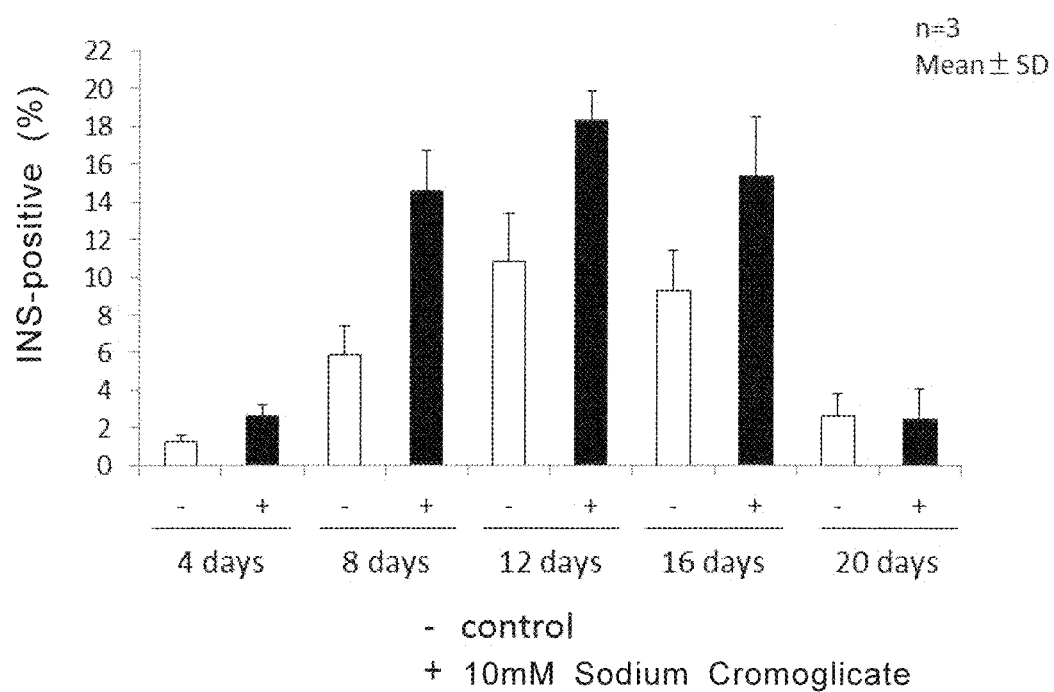
FIG. 2B The iPS cells were treated with 10 mM sodium cromoglicate for 4, 8, 12, 16 and 20 days. The percentages of the insulin positive cells are shown.

In step 3, the cells from 201B7 were cultured 4 days, 8 days, 12 days, 16 days and 20 days and confirmed that the ratio of insulin positive cells was increased in the groups cultured for 8 days, 12 days and 16 days in step 3. The highest ratio of the insulin positive cells was obtained by 12 days-culture in step 3. On the other hand, when cells were cultured for 4 days in step 3, the effect of sodium cromoglicate was also confirmed, although the efficiency was low. (FIG. 2B)

Figure 3:
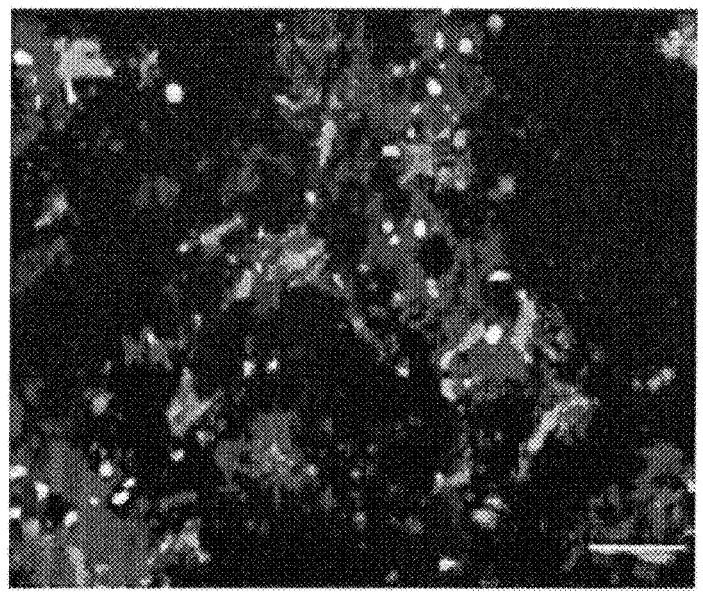
FIG. 3 iPS cells were incubated in a medium supplemented with sodium cromoglicate or in a medium containing no sodium cromoglicate (control). Cells on day 23 were immunostained with anti Ki67 antibody.
Figure 3:
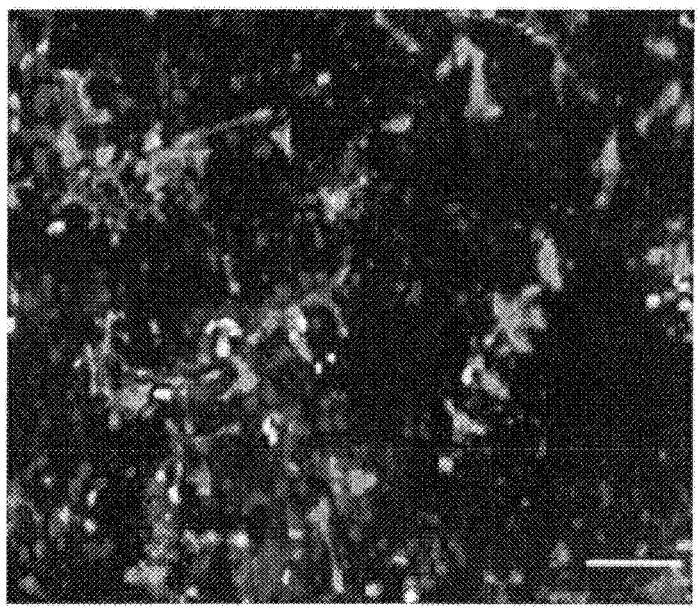
Figure 4:
FIG. 4 iPS cells were incubated in a medium containing sodium cromoglicate or in a medium containing no sodium cromoglicate (control). Cells on day 23 were immunostained with anti-insulin antibody (INS) and anti-glucagon antibody (GCG).
Figure 4:
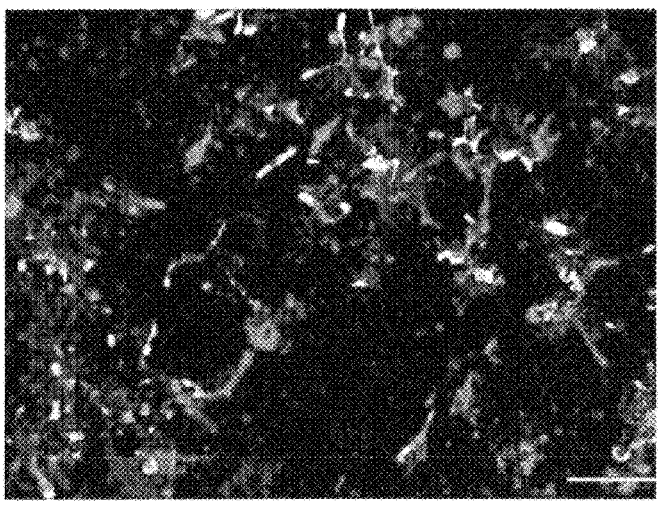

Cells from cell line 201B7 were subjected to steps 1 and 2 in the same manner as above and cultured for 12 days in step 3. The obtained cells were stained with Ki67 and the ability of the cells to proliferate was evaluated. There was no substantial difference in the number of Ki67 positive cells between the cells cultured in the presence and those in the absence of sodium cromoglicate (FIG. 3). This result indicates that the sodium cromoglicate did not enhance the ability of the cells to proliferate. In addition, the obtained cells were treated by using BD Cytofix/Cytoperm™ Kit and stained with monoclonal anti-glucagon clone K79bB10 (SIGMA). The cells were analyzed by flow cytometry to determine the number of the glucagon positive cells. The result showed that the addition of sodium cromoglicate increased the ratio of both insulin positive cells and glucagon positive cells (FIG. 4).

According to the results of example 3, addition of sodium cromoglicate in step 3 promoted not only differentiation into insulin producing cells but also into glucagon producing cells. It was confirmed that the latter effect is separate from proliferation of the insulin producing cells.

Example 4

Examination of Another Condition

Figure 5A:
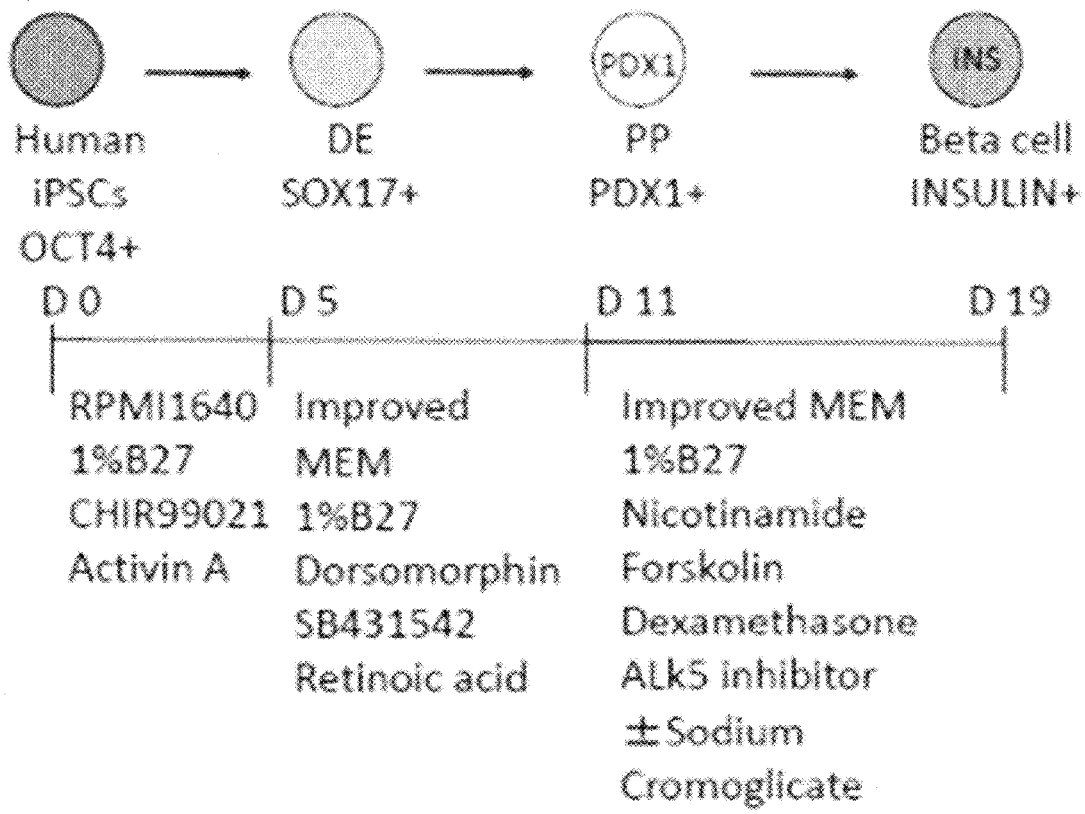
FIG. 5A Scheme for inducing differentiation into β cells from pluripotent stem cells.

Human iPS cell line 201B7 was used. The cells were differentiated into insulin producing cells by the following steps. The colonies of the iPS cell line was grown to 80-90% confluence in the culture plate and dissociated from the dish by using CTK solution (Reprocell). The dissociated colonies were then divided into single cells using Accutase™ and seeded in 24 well plates (Greiner) at $2.0\times10^5$/well.
<Step 1>
The cells were cultured in RPMI medium containing 1% B-27 added with activin A (100 ng/ml), CHIR99021 (1 μM) and Y-27632 (10 μM) for 2 days. Then, the cells were further cultured in RPMI medium containing 1% B-27 added with activin A (100 ng/ml) and CHIR99021 (1 μM) for more 3 days (Day 5). During this period, the medium was changed with the same fresh medium on the third (Day 3) and the fourth days (Day 4).
<Step 2>
The cells obtained in Step 1 were cultured in improved MEM Zinc Option medium containing 1% B-27 added with dorsomorphin (1 μM), retinoic acid (2 μM), and SB431542 (10 μM) for 6 days (Day 11). During this period, the medium was changed with the same fresh medium every two days.
<Step 3>
The cells obtained in Step 2 were cultured in improved MEM Zinc Option medium containing 1% B-27 added with forskolin (10 μM), nicotinamide (10 mM), dexamethasone (10 μM), ALK5 inhibitor II ((2-(3-(6-Methylpyridin-2-yl)-1H-pyrazol-4-yl)-1,5-naphthyridine)) (5 μM) and sodium cromoglicate (10 mM) for more 8 days (Day 19). During this period, the medium was changed with the same fresh medium every four days. The steps are summarized in FIG. 5A.

Figure 5B:
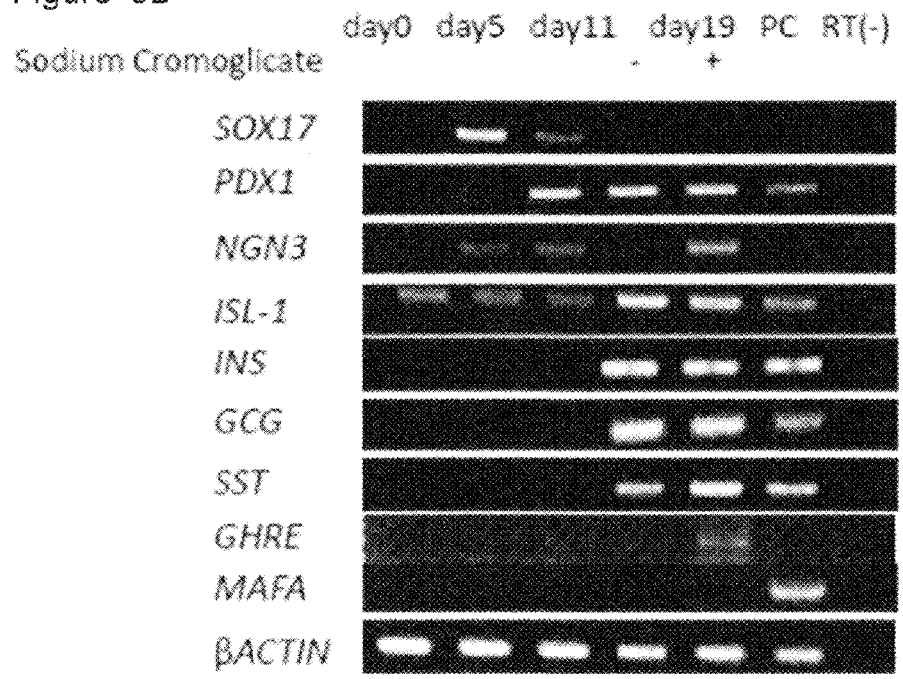
FIG. 5B Expression of marker genes of SOX17, PDX1, NGN3, ISL-1, INS, GCG, SST, GHRE and MAFA on Day 0, Day 5, Day 11 and Day 19 of differentiation.

The cells at each step were collected, i.e. on Day 0, Day 5, Day 11 and Day 19, and the expressions of marker genes were determined by PCR (FIG. 5B). In the group where cells were cultured in the presence of sodium cromoglicate in step 3, the expression of NGN3 and GHRE (Ghrelin) were confirmed. The expression of SST (somatostatin) in the group where cells were cultured in the presence of sodium cromoglicate in step 3 was higher than that in the group where cells were cultured in the absence of sodium cromoglicate.

Figure 5C:
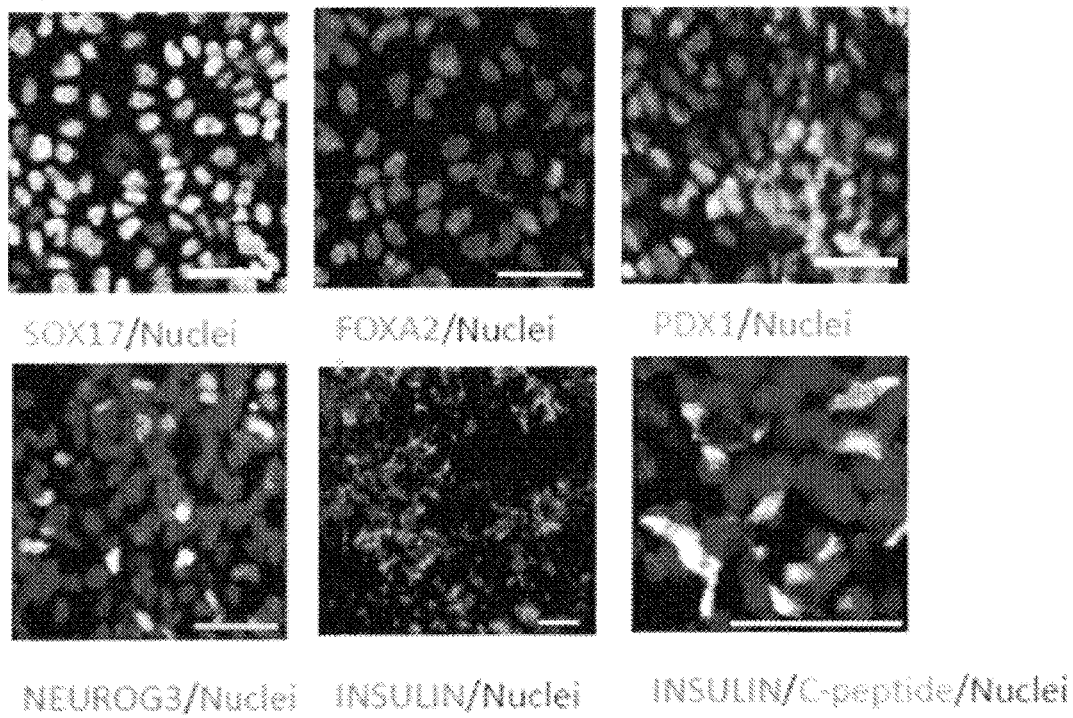
FIG. 5C Cells were immunostained with SOX 17 or FOX A2 on day 5 of the differentiation, with PDX1 on day 11 of the differentiation, NUEROG3 on day 15 of the differentiation and INSULIN or C-peptide on day 19 of the differentiation.
Figure 5D:
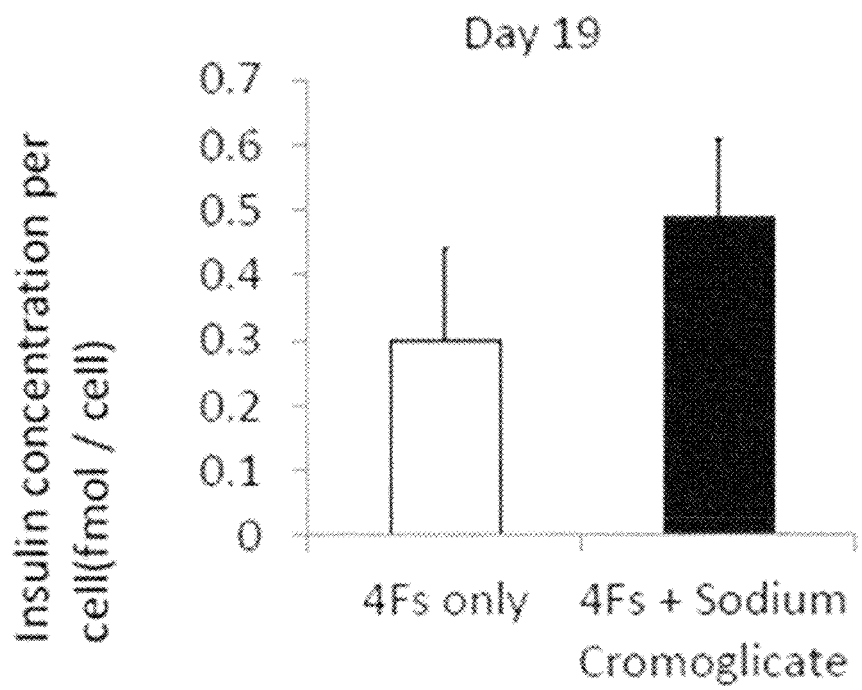
FIG. 5D Cells were differentiated by culturing them in a medium added with four factors (4Fs) consisting of forskolin (10 μM), nicotinamide (10 mM), dexamethasone (10 μM), ALK5 inhibitor II (5 μM) or in a medium added with the 4Fs and sodium cromoglicate. On day 19 of the culture, the insulin concentration per cell was determined.

Further, the cells were subjected to immune staining and confirmed the production of proteins corresponding to the marker genes (FIG. 5C). The amount of insulin produced by the cells obtained by culturing the cells in the presence of sodium cromoglicate in step 3 and that produced by the cells obtained by culturing in the absence of sodium cromoglicate were compared, and the amount of insulin produced by the cells obtained with sodium cromoglicate was higher than that produced by the cells obtained without sodium cromoglicate (FIG. 5D).

Figure 6A:
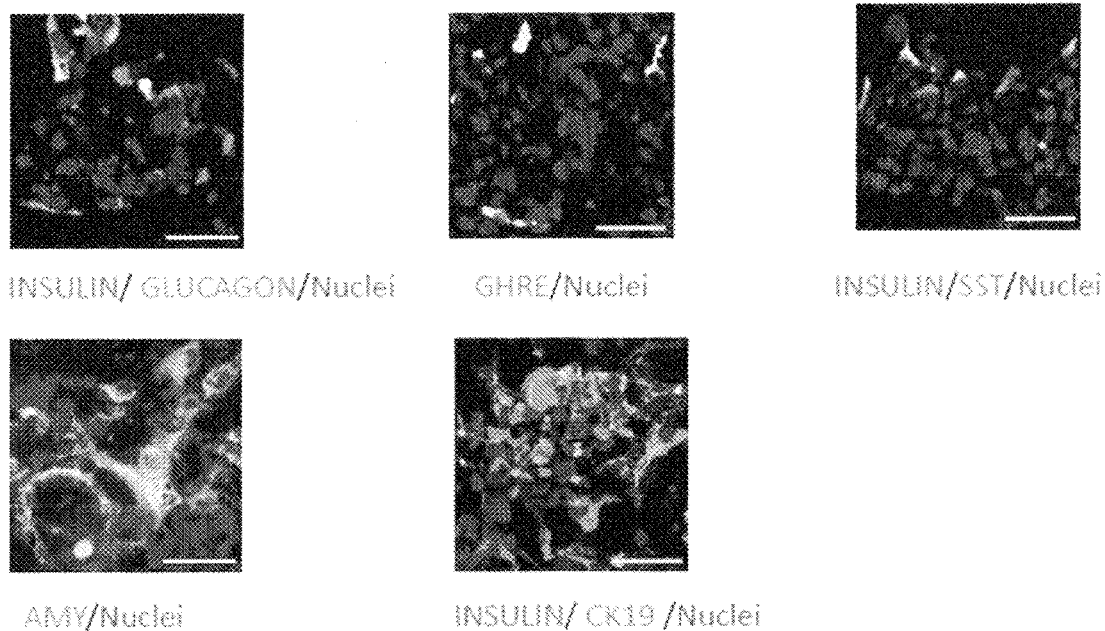
FIG. 6A Cells on day 19 of differentiation were immunostained for insulin, glucagon, GHRE (ghrelin), SST (somatostatin), AMY (amylase) and CK19.
Figure 6B:
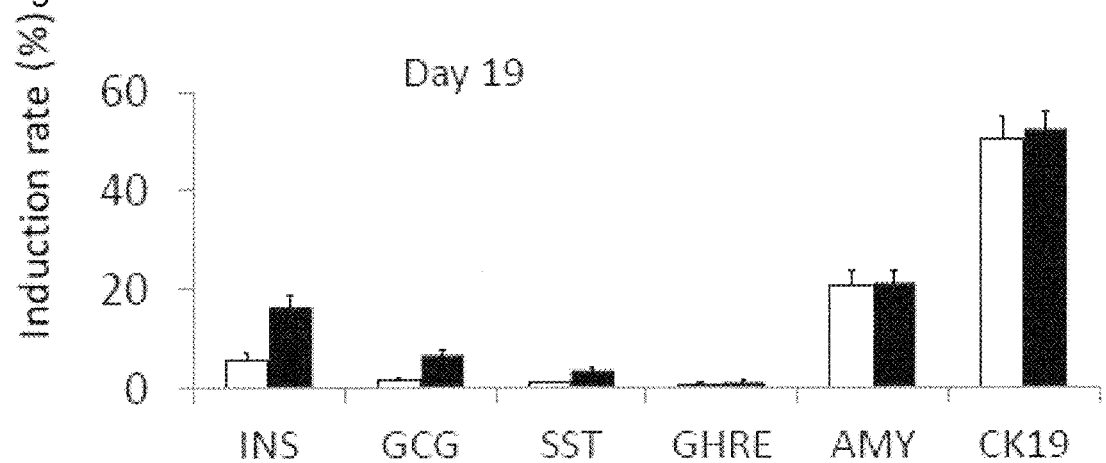
FIG. 6B The percentages of INS (insulin), GCG (glucagon), SST, GHRE, AMY and CK19 positive cells among the cells on day 19 of differentiation were determined.

The cells were subjected to immune staining and the production of pancreatic hormones was confirmed (FIGS. 6A and 6B). The results showed that the expression of insulin, glucagon and somatostatin were increased by culturing the cells in step 3 in the presence of sodium cromoglicate.

As evidenced above, the process in which the cells in step 3 are cultured for 8 days differentiate the cells into pancreatic hormone-producing cells.

Example 5

Differentiation of Fetal Cells into Insulin Producing Cells

Figure 7A:
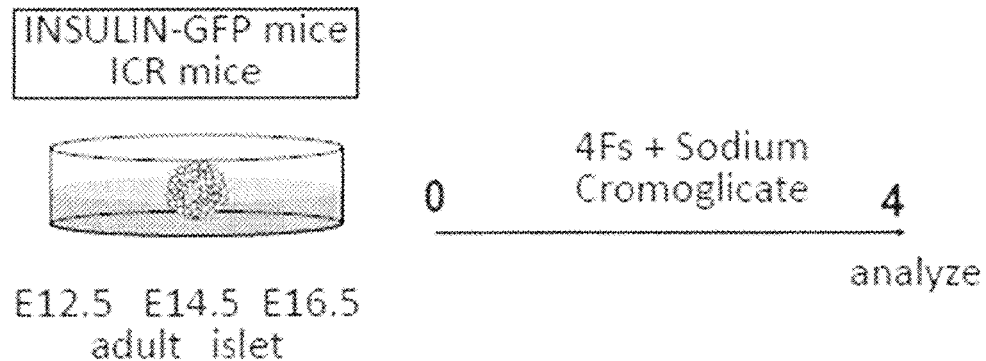
FIG. 7A Scheme for differentiating cells of the pancreatic anlage into insulin-producing cells.

Pancreatic anlages were obtained from mice embryos E12.5, E14.5 and E16.5 that express GFP on the downstream of the insulin promoter. Each pancreatic anlage was cultured in a suspension culture in Improved MEM Zinc Option medium containing 1% B-27 added with forskolin (10 μM), nicotinamide (10 mM), dexamethasone (10 μM), ALK5 inhibitor II (5 μM) and sodium cromoglicate (10 mM) for 4 days. The scheme is summarized in FIG. 7A.

Figure 7B:
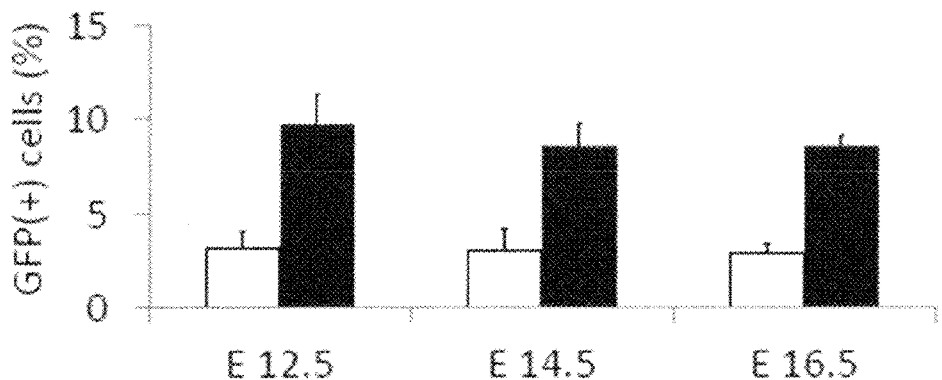
FIG. 7B Cells of pancreatic anlage E12.5, E14.5 and E16.5 were cultured in the presence (black) or absence (white) of sodium cromoglicate and the percentages of GFP (insulin) positive cells were determined.
Figure 7C:
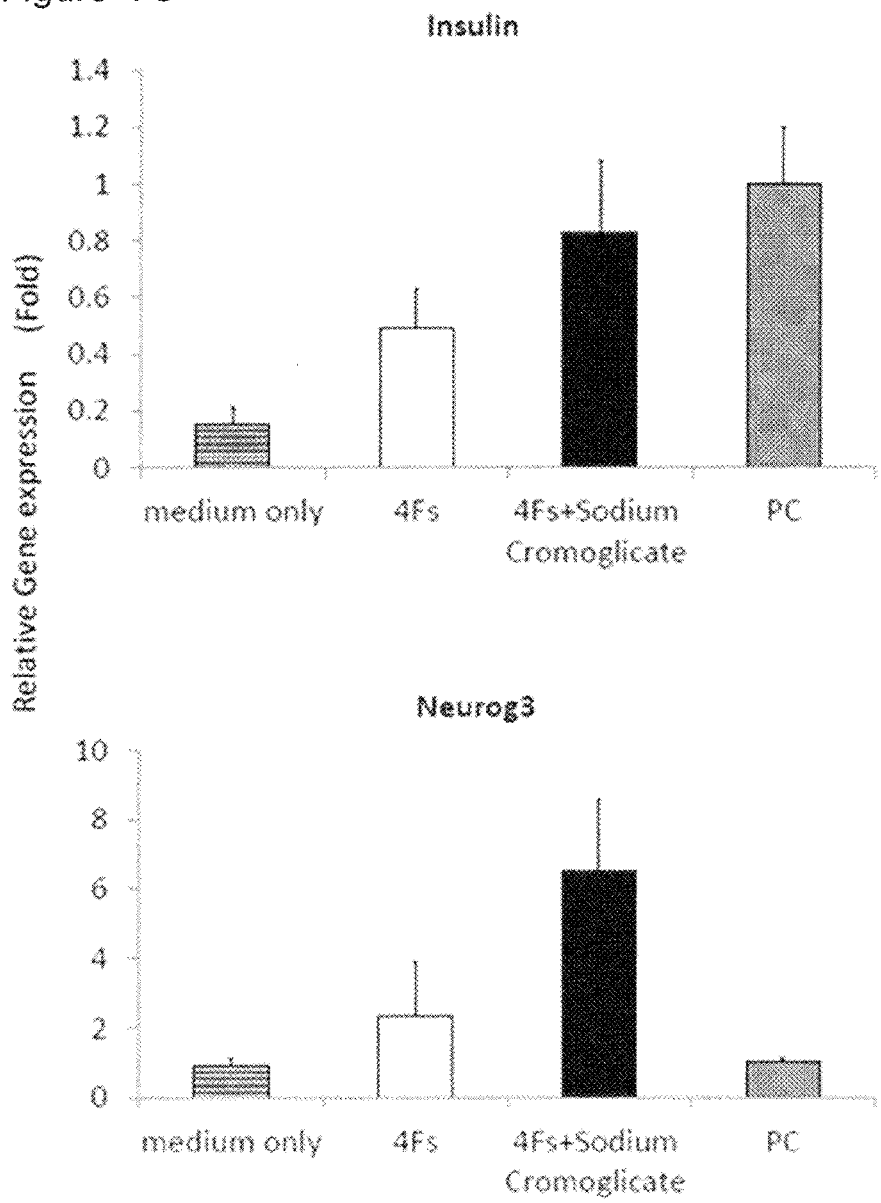
FIG. 7C Cells of pancreatic anlage E12.5, E14.5 and E16.5 were cultured in the basal medium added with 4Fs consisting of forskolin (10 μM), nicotinamide (10 mM), dexamethasone (10 μM) and ALK5 inhibitor II (5 μM), in the basal medium added with 4Fs and sodium cromoglicate or in the basal medium containing no supplement. The amount of insulin and Neurog3 expressed in the resulting cells were determined. In this figure, PC represents positive control that is the amount of insulin and Neurog3 expression in mouse adult pancreatic cells.

The results showed that the addition of sodium cromoglicate increased the ratio of GFP positive cells in each embryonic pancreatic anlage (FIG. 7B). Further, expression of insulin and Neurog 3 in thus obtained cells were analyzed by PCR and confirmed that the expression of those genes was increased in the cells cultured with sodium cromoglicate (FIG. 7C).

According to Example 5, sodium cromoglicate has an effect to promote the differentiation of pancreatic anlages obtained from the living body into insulin producing cells.

Example 6

Examination of the Effect of Sodium Cromoglicate when Used Solely

Human iPS cell line 201B7 was used. The cells were differentiated into insulin producing cells by the following steps. The colonies of the iPS cell line was grown to approximately 80-90% confluence in the culture plate and dissociated from the plate by using CTK solution (Reprocell). The dissociated colonies were then divided into single cells using Accutase™ and seeded in 24 well plates (Greiner) at $2.0\times10^5$/well.
<Step 1>
The cells were cultured in RPMI medium containing 1% B-27 added with activin A (100 ng/ml), CHIR99021 (1 μM) and Y-27632 (10 μM) for 2 days. Then, the cells were further cultured in RPMI medium containing 1% B-27 added with activin A (100 ng/ml) and CHIR99021 (1 μM) for more 3 days (Day 5). During this period, the medium was changed with the same fresh medium on the third (Day 3) and the fourth days (Day 4).

<Step 2>

The cells obtained in Step 1 were cultured in improved MEM Zinc Option medium containing 1% B-27 added with dorsomorphin (1 μM), retinoic acid (2 μM), and SB431542 (10 μM) for 6 days (Day 11). During this period, the medium was changed with the same fresh medium every two days.

<Step 3>

Figure 8A:
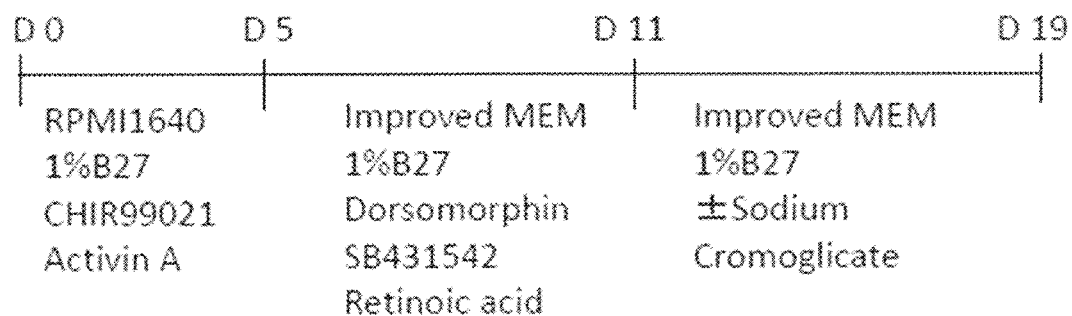
FIG. 8A Scheme for generating β-cells from pluripotent stem cells.

The cells obtained in Step 2 were cultured in improved MEM Zinc Option medium containing 1% B-27 added with sodium cromoglicate (10 mM) for more 8 days (Day 19). During this period, the medium was changed with the same fresh medium every four days. The scheme is summarized in FIG. 8A.

Figure 8B:
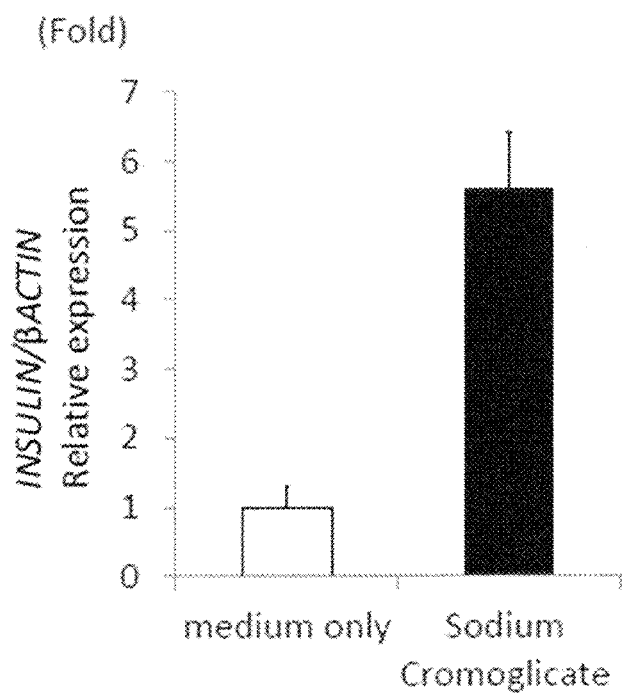
FIG. 8B Cells were cultured in the presence (black) or absence (white) of sodium cromoglicate and the ratio of insulin expression to β-ACTIN expression were determined.
Figure 8C:
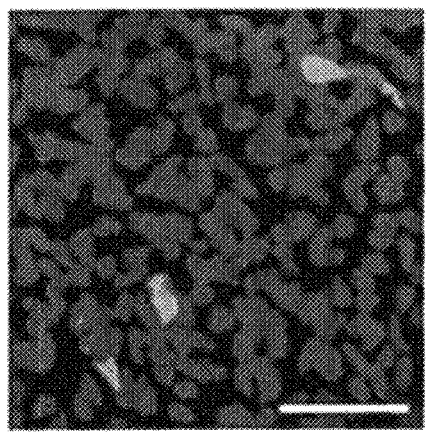
FIG. 8C Cells were cultured in the medium containing sodium cromoglicate (indicated as "Sodium Cromoglicate") or the medium containing no sodium cromoglicate (indicated as "Medium Only") and stained for insulin and nuclei.
Figure 8C:
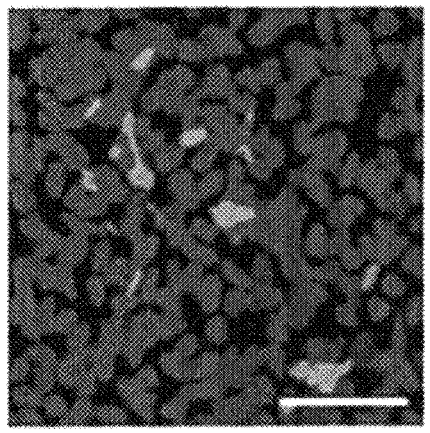
Figure 8D:
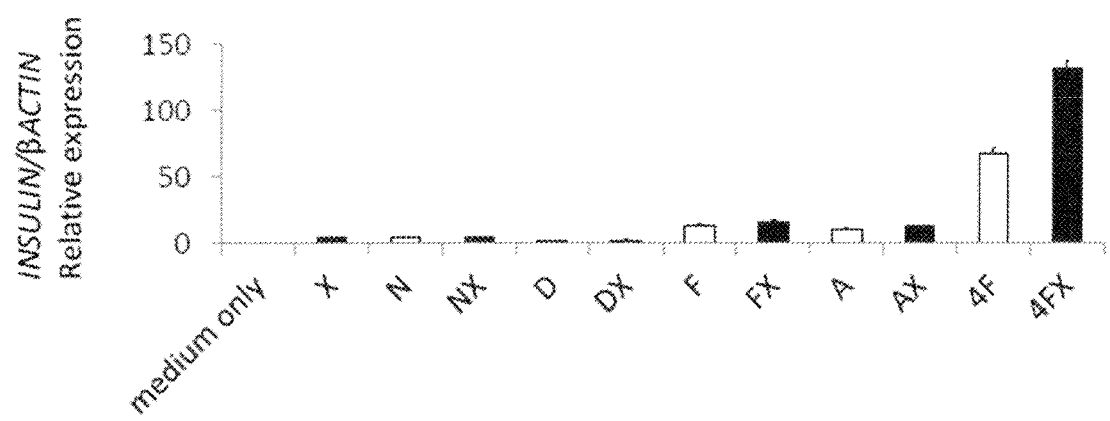
FIG. 8D Cells were cultured in the presence of only sodium cromoglicate (X), only nicotinamide (N), nicotinamide and sodium cromoglicate (NX), only dexamethasone (D), dexamethasone and sodium cromoglicate (DX), only forskolin (F), forskolin and sodium cromoglicate (FX), only ALK5 inhibitor II (A), ALK inhibitor and sodium cromoglicate (AX), 4F or 4F and sodium cromoglicate (4FX) and the ratio of insulin expression to β-ACTIN expression were determined.

The ratio of insulin expression versus β-Actin expression was determined by using quantitative PCR. The results showed that the ratio was higher in the group cultured in the presence of sodium cromoglicate than those cultured in the absence of sodium cromoglicate (FIG. 8B). Further, immune staining of the cells showed that the amount of insulin positive cells was higher in the group where the cells were cultured in the presence of sodium cromoglicate group (FIG. 8C).

Then, the effect of sodium cromoglicate when used in combination with each of the four additives used in EXAMPLE 4: forskolin (10 μM), nicotinamide (10 mM), dexamethasone (10 μM), and ALK5 inhibitor II (5 μM) was determined. Expression of insulin was confirmed in all 4 combinations, although the amount of the expression was not so high. The sodium cromoglicate enhances the effects of all 4 agents for inducing insulin producing cells when used in combination with the agent.

In conclusion, sodium cromoglicate enhances the efficiency to induce insulin producing cells even when it is used alone.

INDUSTRIAL APPLICABILITY

As explained in detail, the present application provides a method for inducing pancreatic hormone-producing cells from pluripotent stem cells. The pancreatic hormone-producing cells prepared by this method may be used for the regenerative treatment of a pancreatic disease, especially, type 1 diabetes.

The invention claimed is:

1. A method for generating pancreatic hormone-producing cells, which comprises culturing pancreas progenitor cells in a medium comprising sodium cromoglicate.

2. The method of claim 1, wherein the medium further comprises at least one agent selected from the group consisting of:
    (a) an cAMP analog;
    (b) nicotinamide;
    (c) a steroid; and
    (d) a TGFβ inhibitor.

3. The method of claim 1, wherein the medium further comprises:
    (a) at least one agent selected from the group consisting of an adenylate cyclase activator, a cAMP phosphodiesterase inhibitor and an cAMP analog;
    (b) nicotinamide;
    (c) a steroid; and
    (d) a TGFβ inhibitor.

4. The method of claim 2, wherein the cAMP analog is forskolin.

5. The method of claim 2, wherein the steroid is dexamethasone.

6. The method of claim 2, wherein the TGFβ inhibitor is 2-(3-(6-Methylpyridin-2-yl)-1H-pyrazol-4-yl)-1,5-naphthyridine.

7. The method of claim 1, wherein the pancreatic progenitor cells are the cells derived from a method comprising the following steps:
    (1) culturing pluripotent stem cells in a medium comprising an activator of activin receptor-like kinase-4,7 and a GSK3 inhibitor, and
    (2) culturing the cells obtained in step (1) in a medium comprising (a) a retinoic acid receptor agonist, (b) a BMP inhibitor and (c) a TGFβ inhibitor.

8. The method of claim 7, wherein the activator of activin receptor-like kinase-4,7 is activin.

9. The method of claim 7, wherein the GSK3 inhibitor is CHIR99021.

10. The method of claim 7, wherein the TGFβ inhibitor used in step (2) is SB431542.

11. The method of claim 7, wherein the BMP inhibitor is dorsomorphin.

12. The method of claim 1, wherein the pancreatic hormone-producing cells are selected from the group consisting of insulin producing cells, glucagon producing cells, somatostatin producing cells and pancreatic polypeptide producing cells.

13. The method of claim 12, wherein the pancreatic hormone-producing cells are insulin producing cells and/or glucagon producing cells.

14. The method of claim 1, wherein the pancreatic progenitor cells are human cells.

15. The method of claim 1, wherein the medium further comprises at least one agent selected from the group consisting of:
    (a) an adenylate cyclase activator;
    (b) nicotinamide;
    (c) a steroid; and
    (d) a TGFβ inhibitor.

16. The method of claim 15, wherein the steroid is dexamethasone.

17. The method of claim 15, wherein the TGFβ inhibitor is 2-(3-(6-Methylpyridin-2-yl)-1H-pyrazol-4-yl)-1,5-naphthyridine.

18. The method of claim 1, wherein the medium further comprises at least one agent selected from the group consisting of:
    (a) a cAMP phosphodiesterase inhibitor;
    (b) nicotinamide;
    (c) a steroid; and
    (d) a TGFβ inhibitor.

19. The method of claim 18, wherein the steroid is dexamethasone.

20. The method of claim 18, wherein the TGFβ inhibitor is 2-(3-(6-Methylpyridin-2-yl)-1H-pyrazol-4-yl)-1,5-naphthyridine.

* * * * *